United States Patent
Kimura et al.

(10) Patent No.: US 8,518,841 B2
(45) Date of Patent: Aug. 27, 2013

(54) STRETCHABLE NONWOVEN FABRIC AND TAPE

(75) Inventors: Tomoaki Kimura, Osaka (JP); Yasuro Araida, Osaka (JP); Toru Ochiai, Okayama (JP); Sumito Kiyooka, Okayama (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 275 days.

(21) Appl. No.: 12/376,361

(22) PCT Filed: Jul. 27, 2007

(86) PCT No.: PCT/JP2007/064763
§ 371 (c)(1),
(2), (4) Date: Feb. 4, 2009

(87) PCT Pub. No.: WO2008/015972
PCT Pub. Date: Feb. 7, 2008

(65) Prior Publication Data
US 2010/0035500 A1    Feb. 11, 2010

(30) Foreign Application Priority Data
Aug. 4, 2006    (JP) ................................. 2006-212828

(51) Int. Cl.
*D04H 1/06*    (2012.01)
(52) U.S. Cl.
USPC ......... 442/352; 428/293.7; 442/353; 442/361
(58) Field of Classification Search
USPC ...................... 442/353, 361, 352; 428/293.7
See application file for complete search history.

(56) References Cited

U.S. PATENT DOCUMENTS 3,639,154 A * 2/1972 Sawa et al. ..................... 442/102
5,569,525 A * 10/1996 Masuda et al. ................ 428/219
(Continued)

FOREIGN PATENT DOCUMENTS

CN    1606640 A    4/2005
DE    198 04 418 A1    8/1999
(Continued)

OTHER PUBLICATIONS

"Polybutylene terephthalate," Encyclopaedia Britannica, found online at www.britannica.com.*

(Continued)

*Primary Examiner* — Peter Y Choi
(74) *Attorney, Agent, or Firm* — Oblon, Spivak, McClelland, Maier & Neustadt, L.L.P.

(57) ABSTRACT

To produce a nonwoven fabric comprising a conjugated fiber comprising a plurality of resins which are different in thermal shrinkage and form a phase separation structure. In the nonwoven fabric, the conjugated fibers are arranged in a direction approximately parallel to a surface direction of the nonwoven fabric and crimped. In addition, the conjugated fibers have an average curvature radius of fiber crimp of 20 to 200 µm and the crimps are distributed approximately uniformly in a thickness direction of the nonwoven fabric. The nonwoven fabric is substantially free from an adhesive agent. In the nonwoven fabric, each fiber is substantially not melt-bonded to another. The conjugated fiber may comprise a polyalkylene arylate-series resin and a modified polyalkylene arylate-series resin and have a side-by-side or eccentric sheath-core form. Since the bimetal form conjugated fibers having specific crimps are appropriately entangled with each other, the nonwoven fabric has a high stretchability and is easily torn by hand, without using scissors. The nonwoven fabric is suitable for a tape such as a bandage or a supporter.

18 Claims, 4 Drawing Sheets

(a)

(b)

(56) References Cited

U.S. PATENT DOCUMENTS

| | | | |
|---|---|---|---|
| 6,632,504 B1 * | 10/2003 | Gillespie et al. | 428/131 |
| 2002/0037408 A1 | 3/2002 | Tsutsui et al. | |
| 2005/0095943 A1 * | 5/2005 | Griffin et al. | 442/352 |

FOREIGN PATENT DOCUMENTS

| | | |
|---|---|---|
| EP | 1 417 946 A1 | 5/2004 |
| GB | 1 423 213 | 2/1976 |
| JP | 48 309 | 1/1973 |
| JP | 63 68163 | 3/1988 |
| JP | 63 260553 | 10/1988 |
| JP | 63 270102 | 11/1988 |
| JP | 1 190358 | 7/1989 |
| JP | 6 321610 | 11/1994 |
| JP | 11 89874 | 4/1999 |
| JP | 2002 38363 | 2/2002 |
| JP | 2002 88583 | 3/2002 |
| JP | 2003 514105 | 4/2003 |
| JP | 3473561 B2 | 12/2003 |
| JP | 2004 124351 | 4/2004 |
| JP | 2005 95381 | 4/2005 |
| JP | 2006 507417 | 3/2006 |
| WO | WO 03/040452 A1 | 5/2003 |
| WO | WO 03/056086 A1 | 7/2003 |
| WO | 2004 033780 | 4/2004 |
| WO | WO 2004046442 A1 * | 6/2004 |

OTHER PUBLICATIONS

"Polyethylene terephthalate," IFA Gestis—Substance Database, found online at biade.itrust.de.*

Chinese Office Action issued on Aug. 4, 2010 in corresponding Chinese Application No. 200780036395.9 filed on Jul. 27, 2007 (with English Translation).

Extended European Search Report issued Apr. 29, 2011, in Patent Application No. 07791457.0.

* cited by examiner (1)

(2)

(a)                      (b)

STRETCHABLE NONWOVEN FABRIC AND TAPE

TECHNICAL FIELD

The present invention relates to a nonwoven fabric which is easy to tear and has stretchability and self-fastenability. The nonwoven fabric is suitable for a tape used in medical or sport field (such as a bandage or a supporter).

BACKGROUND ART

In medical and sport fields, various tapes such as bandages and supporters have conventionally been used for compressing, immobilizing (or fixing), or protecting a body part (e.g., a limb and an affected area or part) properly by applying the tapes on the body part. These tapes require properties such as fastenability (e.g., a self-fastenability due to only contacting the surfaces of tape with each other and a fastenability due to an adhesive agent), in addition to stretchability or conformability, sweat-absorbability, and air-permeability. In order to achieve the properties mentioned above, in particular, stretchability or fastenability, a soft component such as a rubber-series or acrylic latex is usually applied on a surface of a bandage (see Patent Documents 1 to 5). However, the soft component possibly causes a skin irritation or an unpleasantly humid (or steamy) and warm state of the area covered with the tape due to a reduced air flow through the tape. Possibly, an allergy is also induced. In terms of safety, the tapes mentioned above are undesirable.

In order to reduce irritation to skin, a medical material using a natural rubber latex containing a small amount of protein as an adhesive agent (see Patent Document 6) or an self-adhesive bandage using a specific acrylic polymer as an adhesive agent (see Patent Document 7) has been proposed. However, since the medical materials disclosed in the patent documents also use the adhesive agent after all, the fact is that the drawbacks have not been eliminated drastically.

As mentioned above, there has not been a product such as a bandage or a supporter, satisfying both a sufficient self-fastenability and an appropriate stretchability without an adhesive agent. Most of the conventional products are torn by hand in a length direction of the product. A tape which can be torn by one hand easily and whose end formed by tearing can easily be fixed in place on a surface of the underlying tape has not been developed yet.

[Patent Document 1] JP-48-000309B
[Patent Document 2] JP-63-068163A
[Patent Document 3] JP-63-260553A
[Patent Document 4] JP-01-190358A
[Patent Document 5] JP-11-089874A
[Patent Document 6] JP-2003-514105A
[Patent Document 7] JP-2005-095381A

DISCLOSURE OF THE INVENTION

Problems to be Solved by the Invention

It is therefore an object of the present invention to provide a nonwoven fabric and a tape which are easy to tear by hand and has stretchability.

Another object of the present invention is to provide a nonwoven fabric and a tape which can be self-fastened easily and firmly, without using an adhesive agent, by overlapping an end thereof in place on the surface of the underlying nonwoven fabric.

A further object of the present invention is to provide a tape (such as a bandage or a supporter) which has air-permeability and a less irritation to skin and can easily be torn across the width direction to use for immobilizing a limb or an affected area easily.

Means to be Solve the Problems

The inventors of the present invention made intensive studies to achieve the above objects and finally found that a nonwoven fabric obtained by subjecting a conjugated (or composite) fiber potentially capable (or a conjugated (or composite) fiber having a latent ability of crimping by heating to a high-temperature water vapor (or to a high-temperature moisture) to develop a three-dimensional crimp and to allow the crimped fiber to entangle with another is stretchable (or stretchy) and easy to tear by hand. The present invention has achieved based on the findings.

That is, the nonwoven fabric of the present invention comprises a conjugated fiber comprising a plurality of resins which are different in thermal shrinkage and form a phase separation structure. In the nonwoven fabric, the conjugated fibers are arranged in a direction approximately parallel to a surface direction of the nonwoven fabric and crimped. In addition, the conjugated fibers have an average curvature radius of fiber crimp of 20 to 200 μm and the crimps are distributed approximately uniformly in a thickness direction of the nonwoven fabric. The resin constituting the conjugated fiber may comprise a non thermal adhesive resin under moisture which has a softening point or melting point of not lower than 100° C. and forms at least a portion of a surface of the conjugated fiber. The nonwoven fabric of the present invention may be a nonwoven fabric which is substantially free from an adhesive agent and in which each fiber is substantially not melt-bonded to another. The conjugated fiber may comprise a polyalkylene arylate-series resin and a modified polyalkylene arylate-series resin and have a parallel (a side-by-side) or eccentric sheath-core form. In the above-mentioned nonwoven fabric the proportion of the conjugated fiber may be not less than 80% by mass. The nonwoven fabric of the present invention may have a plurality of low-density portions and a plurality of high-density portions in a surface direction. The low-density portion and the high-density portion may be alternately formed in a periodic pattern. In addition, the nonwoven fabric mentioned above may have a strength at break of about 5 to 30 N/50 mm, an elongation at break of not less than 50%, a recovery after 50% elongation of not less than 80%, and a slip stress at curved surfaces in contact of not less than 0.5 N/50 mm, in at least one direction. Moreover, the nonwoven fabric may have a curved ratio of fiber of not less than 1.3 in each of three areas and a proportion of the minimum curved ratio of fiber relative to the maximum curved ratio of fiber, for example, not less than 75% in each of the three areas, providing that the nonwoven fabric is cut across the thickness direction and the cross section is divided in a direction perpendicular to the thickness direction equally into three. The nonwoven fabric of the present invention may have a tape- or band-like form and a ratio of the streng that breakin a length direction relative to the strength at break in a width direction of about 1.5 to 50. The nonwoven fabric of the present invention may be a tape such as a bandage or a supporter. The nonwoven fabric of the present invention may be a nonwoven fabric obtained by a process for producing a nonwoven fabric comprising a step for forming a web with a fiber including a conjugated fiber comprising a plurality of resins which are different in thermal shrinkage and form a phase separation structure and a step for heating the resulting fiber web with a high-temperature water vapor to allow the conjugated fiber to develop a crimp having an average curvature radius of 20 to 200 μm.

The present invention includes a process for producing the nonwoven fabric which comprises a step for forming a web with a fiber including a conjugated fiber comprising a plurality of resins which are different in thermal shrinkage and form a phase separation structure and a step for heating the resulting fiber web to allow the conjugated fiber to develop a crimp. The production process may further comprise a step for entangling the fibers in an area of the fiber web loosely before the step for heating the resulting fiber web with a high-temperature water vapor to allow the conjugated fiber to develop a crimp.

Effects of the Invention

Since the nonwoven fabric of the present invention comprises conjugated (composite) fibers forming specific crimps and entangled with each other appropriately, the nonwoven fabric has a high stretchability and is easy to tear by hand, without using a pair of scissors or the like. In addition, since the nonwoven fabric can be self-fastened easily and firmly by overlapping an end or the like thereof in place on a surface of the underlying nonwoven fabric without using an adhesive agent, the nonwoven fabric can be used safely for the human body without using a skin irritating material (e.g., a latex harmful for the human body). The nonwoven fabric of the present invention is thus suitable for a tape used for applications where the tape contacts with the human body. Since the nonwoven fabric of the present invention has air-permeability in addition to the properties mentioned above, the nonwoven fabric is suitable for a tape (such as a bandage or a supporter). Moreover, a tape prepared from the nonwoven fabric can be torn across the width direction easily, and the end formed by tearing the tape is fastened in place on a surface of the underlying tape.

Incidentally, the term "be self-fastened" in the present specification means that a tape- or belt-shaped nonwoven fabric is fastened, without using an auxiliary part or an adhesive agent, by overlapping an end or the like of the nonwoven fabric with a surface of the underlying nonwoven fabric to engage the nonwoven fabric surfaces with each other as if both sides of a hook and loop fastener couple or join together.

DETAILED DESCRIPTION OF THE INVENTION

[Nonwoven Fabric]

Figure 1:
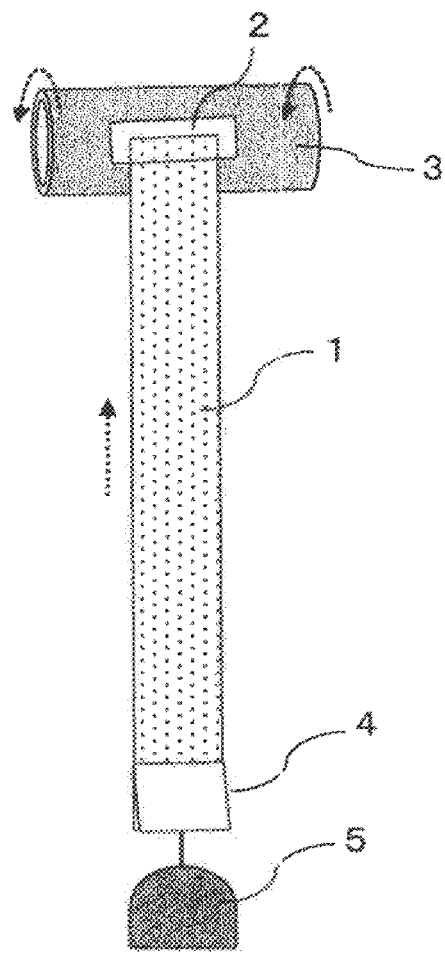
FIG. 1 is a schematic diagram showing a manner of preparing a sample to be used for determination of a slip stress at curved surfaces in contact in the present invention.
Figure 1:
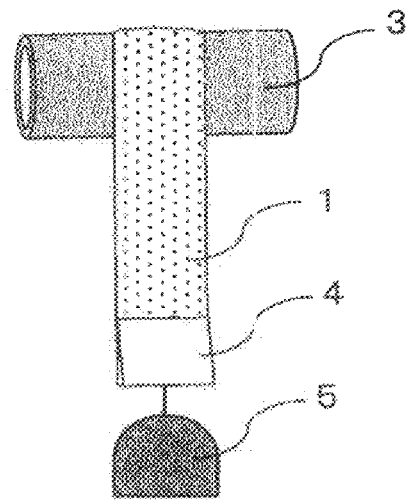

The nonwoven fabric of the present invention comprises a conjugated fiber comprising a plurality of resins which are different in thermal shrinkage (or thermal expansion) and form a phase separation structure. In the nonwoven fabric, the conjugated fibers are arranged with putting the length direction thereof mainly in a direction parallel to the nonwoven fabric surface and are crimped. The fiber crimp is developed along with a direction horizontal to the nonwoven fabric surface and has an average curvature radius of 20 to 200 μm. As described later in detail, the nonwoven fabric is obtainable by subjecting a web comprising the conjugated fibers to a high-temperature water vapor (a super-heated or heated water vapor) or by treating a web comprising the conjugated fiber with a high-temperature (a super-heated or heated) moisture or steam to develop the crimps of the conjugated fibers and to entangle the conjugated fibers with each other (mechanically) without melt-bonding the fibers.

(Material for Nonwoven Fabric)

The conjugated fiber is a fiber comprising a plurality of resins different in thermal shrinkage (or thermal expansion) and has an asymmetric or layer structure (such as a bimetal-like structure) formed from the plurality of resins (a potential crimping fiber). When the conjugated fiber is heated, the crimps thereof are developed due to the difference in thermal shrinkage. The plurality of resins are usually different in softening point or melting point. Such resins may be selected from a thermoplastic resin, for example, a polyolefinic resin (e.g., a poly$C_{2-4}$olefinic resin such as a low-density polyethylene, a middle-density polyethylene or a high-density polyethylene, or a polypropylene), an acrylic resin (e.g., an acrylonitrile-series resin having an acrylonitrile unit such as an acrylonitrile-vinyl chloride copolymer), a polyvinyl acetal-series resin (e.g., a polyvinyl acetal resin), a polyvinylchloride-series resin (e.g., a polyvinyl chloride, a vinyl chloride-vinyl acetate copolymer, and a vinyl chloride-acrylonitrile copolymer), a polyvinylidene chloride-series resin (e.g., a vinylidene chloride-vinyl chloride copolymer, and a vinylidene chloride-vinyl acetate copolymer), a styrenic resin (e.g., a heat-resistant polystyrene), a polyester-series resin (e.g., a poly$C_{2-4}$alkylene arylate-series resin such as a polyethylene terephthalate resin, a polytrimethylene terephthalate resin, a polybutylene terephthalate resin, and a polyethylene naphthalate resin), a polyamide-series resin (e.g., an aliphatic polyamide-series resin such as a polyamide 6, a polyamide 66, a polyamide 11, a polyamide 12, a polyamide 610, or a polyamide 612, a semiaromatic polyamide-series resin, and an aromatic polyamide-series resin such as a polyphenylene isophthalamide, a polyhexamethylene terephthalamide, or a poly(p-phenylene terephthalamide)), a polycarbonate-series resin (e.g., a bisphenol-A based polycarbonate), a poly(p-phenylenebenzobisoxazole) resin, a poly(phenylene sulfide) resin, a polyurethane-series resin, and a cellulose-series resin (e.g., a cellulose ester). In addition, each thermoplastic resin may contain other copolymerizable unit(s).

Among these resins, the preferred one is a non thermal adhesive resin under moisture (or a heat-resistant hydrophobic resin or non-water-soluble resin) having a softening point or melting point of not lower than 100° C. since the non thermal adhesive resin under moisture neither melt nor soften and does not melt-bonded to the fibers constituting the nonwoven fabric even by the heat treatment with a high-temperature water vapor. Such a non thermal adhesive resin under moisture preferably includes, for example, a polypropylene-series resin, a polyester-series resin, and a polyamide-series resin. The particularly preferred resin includes an aromaticpolyester-series resin or a polyamide-series resin because such a resin has an excellent balance of heat resistance, fiber formability, and the like. In the present invention, in order to prevent each of the fibers constituting the nonwoven fabric from melt-bonding to another in the treatment with a high-temperature water vapor, it is preferable that the non thermal adhesive resin under moisture form at least a portion of surface of the conjugated fiber.

As long as the plurality of resins constituting the conjugated fiber are different in thermal shrinkage, the plurality of resins may be a combination of the same series resins or a combination of different series resins.

In the present invention, in terms of the adhesiveness between the plurality of the resins, a combination of the plurality of the same series resins is preferred. Such a combination of the same series resins usually includes a combination of (A) a homopolymer component (an essential component) and (B) a modified polymer component (a copolymer component). The modified polymer component (B) may be a modified polymer which is obtained by copolymerizing a homopolymer component (i.e., an essential component) the same as the homopolymer component (A) with a copolymerizable monomer (e.g., a copolymerizable monomer used for the copolymerization of the homopolymer in order to lower a degree of crystallization, a melting point, or a softening point of the homopolymer). That is, the modified polymer component (B) may be a modified polymer having a degree of crystallization lower than that of the homopolymer (i.e. the essential component) or an amorphous copolymer having a melting point, a softening point, or the like lower than that of the homopolymer. In this manner, the inherent crystallinity, melting point or softening point of the homopolymer may be changed in order to produce the difference in thermal shrinkage between the resins (the homopolymer and the copolymer). The difference in melting point or softening point may be, for example, 5 to 150° C., preferably 50 to 130° C., and more preferably 70 to 120° C. The proportion of the copolymerizable monomer to be used for the modification of the homopolymer relative to the total monomers in the modified polymer is, for example, about 1 to 50 mol %, preferably about 2 to 40 mol %, and more preferably about 3 to 30 mol % (particularly, about 5 to 20 mol %). The composition rate (mass ratio) of the component (A) relative to the component (B) is selected according to the structure of the conjugated fiber. The composition rate [the homopolymer component (A)/the modified polymer component (B)] is, for example, about 90/10 to 10/90, preferably about 70/30 to 30/70, and more preferably about 60/40 to 40/60.

In order to produce the conjugated fiber of the present invention easily, which has a latent ability to develop crimps, a combination of the aromatic polyester-series resins may be used. In particular, a combination of (a) a polyalkylene arylate-series resin and (b) a modified polyalkylene arylate-series resin may be used. The polyalkylene arylate-series resin (a) may be a homopolymer produced from a polycondensation of an aromatic dicarboxylic acid (e.g., a symmetric aromatic dicarboxylic acid such as terephthalic acid or naphthalene-2,6-dicarboxylic acid) and an alkanediol component (a $C_{2-6}$ alkanediol such as ethylene glycol or butylene glycol). Specifically, a polyC2-4alkylene terephthalate-series resin such as a polyethylene terephthalate (PET) or a polybutylene terephthalate (PBT) is used. The PET usually employed is a PET used for a general PET fiber and having an intrinsic viscosity of about 0.6 to 0.7.

On the other hand, for producing the modified polyalkylene arylate-series resin (b), a copolymerizable component lowering the melting point or softening point, or the degree of crystallization of the polyalkylene arylate-series resin (a), which is the essential component, may be used. Such a copolymerizable component may include, for example, a dicarboxylic acid component such as an asymmetric aromatic dicarboxylic acid, an alicyclic dicarboxylic acid, or an aliphatic dicarboxylic acid, an alkanediol component and/or a diol component which have/has a chain longer than the alkanediol of the polyalkylene arylate-series resin (a). These copolymerizable components may be used alone or in combination. Among these components, the dicarboxylic acid component widely used includes, an asymmetric aromatic dicarboxylic acid (e.g., isophthalic acid, phthalic acid, and sodium 5-sulfoisophthalate), an aliphatic dicarboxylic acid (an aliphatic C6-12dicarboxylic acid such as adipic acid). The diol component widely used includes, an alkanediol (e.g., a C3-6alkanediol such as 1,3-propanediol, 1,4-butanediol, 1,6-hexanediol, or neopentyl glycol), a polyoxyalkylene glycol (e.g., a polyoxyC2-4alkylene glycol such as diethylene glycol, triethylene glycol, a polyethylene glycol, or polytetramethylene glycol). The preferred one includes an asymmetric aromatic dicarboxylic acid such as isophthalic acid, a polyoxyC2-4alkylene glycol such as diethylene glycol, or the like. In addition, the modified polyalkylene arylate-series resin (b) may be an elastomer which has a C2-4alkylene arylate (e.g., ethylene terephthalate and butylene terephthalate) as a hard segment and a (poly)oxyalkylene glycol as a soft segment.

The proportion of the dicarboxylic acid component lowering the melting point or softening point of the homopolymer (e.g., isophthalic acid) relative to the total amount of the dicarboxylic acid components in the modified polyalkylene arylate-series resin (b) is, for example, about 1 to 50 mol %, preferably about 5 to 50 mol %, and more preferably about 15 to 40 mol %. The proportion of the diol component lowering the melting point or softening point of the homopolymer (e.g., diethylene glycol) relative to the total amount of the diol components in the modified polyalkylene arylate-series resin (b) is, for example, not more than 30 mol %, and preferably not more than 10 mol % (e.g., about 0.1 to 10 mol %). An excessively small proportion of the copolymerizable component prevents a sufficient crimp development, whereby after the crimp development, the form stability and stretchability of the nonwoven fabric are deteriorated. On the other hand, an excessively large proportion of copolymerizable component greatly prompts the crimp development. However, such a proportion prevents a stable spinning.

The modified polyalkylene arylate-series resin (b) may have a branched structure, which results from the combination use of a polyalkylene arylate-series resin with a polycarboxylic carboxylic acid component (e.g., trimellitic acid and pyromellitic acid), a polyol component (e.g., glycerin, trimethylolpropane, trimethylolethane, and pentaerythritol), or the like, according to need.

The cross-sectional form of the conjugated fiber (a form or shape of a cross section perpendicular to the length direction of the fiber) may include not only a common solid-core cross section, but also a hollow cross section. Such a common solid-core cross section may include, e.g., a circular cross section or a deformed (or modified) cross section [e.g., a flat form, an oval (or elliptical) form, a polygonal form, a multi-leaves form from tri-leaves to 14-leaves, a T-shaped form, an H-shaped form, a V-shaped form, and a dog-bone form (I-shaped form)]. The conjugated fiber usually has a circular cross section.

The cross-sectional structure of the conjugated fiber may include a phase separation structure comprising a plurality of resins, e.g., a sheath-core form, an islands-in-the-sea form, a parallel form (a side-by-side form or a multi-layer laminated form), a radial form (a radially-laminated form), a hollow radial form, a block form, and a random conjugate form. Among these cross-sectional structures, the preferred one includes a structure having phase adjacent to each other (a structure which is like a bimetal structure) or a structure having phases disposed asymmetrically to each other (e.g., an eccentric sheath-core form and a side-by-side form structure) since the crimps are easily developed by heating.

Incidentally, in a sheath-core form (such as an eccentric sheath-core form) conjugated fiber comprising the non thermal adhesive resin under moisture as the sheath part, which is the outer part of the conjugated fiber, the core part may comprise a thermal adhesive resin under moisture or a thermoplastic resin having a low melting point or softening point as long as the conjugated fiber has a latent ability to develop crimps due to the difference in thermal shrinkage between the sheath part and core parts. Such a thermal adhesive resin under moisture includes, e.g., a vinyl alcohol-series polymer such as an ethylene-vinyl alcohol copolymer or a polyvinyl alcohol. Such a thermoplastic resin includes, e.g., a polystyrene and a low-density polyethylene.

The average fineness of the conjugated fiber may be selected from, for example, the range of about 0.1 to 50 dtex, and may be preferably about 0.5 to 10 dtex, and more preferably about 1 to 5 dtex (particularly, about 1.5 to 3 dtex). A conjugated fiber having an excessively small fineness is difficult to produce and has a low fiber strength. In addition, such a conjugated fiber is difficult to form a continuous and smooth coil in the step for developing crimps. On the other hand, a conjugated fiber having an excessively large fineness is stiff, which makes a sufficient crimp development difficult.

The average fiber length of the conjugated fiber may be selected from, for example, the range of about 10 to 100 mm, and may be preferably about 20 to 80 mm, and more preferably about 25 to 75 mm (particularly, about 40 to 60 mm). An excessively short fiber length makes a fiber web formation difficult and, in the step for developing crimps, causes an insufficient entanglement of the fibers, whereby it is difficult to provide a nonwoven fabric having strength and stretchability. On the other hand, an excessively long fiber length hinders formation of a fiber web having a uniform basic weight. In addition, at the web formation, the resulting fiber web has many fiber entanglements, which hinder the crimp development since the move of the fibers is restrained by the entanglement. Therefore, it is difficult to provide a nonwoven fabric having stretchability. In the present invention, when the conjugated fiber having a fiber length within the range mentioned above is crimped, the crimp of the fiber forming the nonwoven fabric surface partly protrudes from the inside of the nonwoven fabric, which is consequently advantageous to enhancement of the self-fastenability of the nonwoven fabric mentioned later.

Such a conjugated fiber mentioned above develops a crimp (or the crimp of such a conjugated fiber mentioned above is allowed to manifest themselves) by a heat treatment. In the crimp development the form of the fiber changes into a three-dimensional form such as a coil-like form (a spiral form or shape or a helical or coil spring form or shape).

The number of crimps before heating (the number of mechanical crimps) is, for example, about 0 to 30/25 mm, preferably about 1 to 25/25 mm, and more preferably about 5 to 20/25 mm. The number of crimps after heating may be, for example, not less than 30/25 mm (e.g., about 30 to 200/25 mm), preferably about 35 to 150/25 mm, more preferably about 40 to 120/25 mm, and about 45 to 120/25 mm (particularly about 50 to 100/25 mm).

Since the crimp of the fiber is developed with or by a high-temperature water vapor, the nonwoven fabric of the present invention has a feature that the distribution of the crimp of the fiber arranged with putting the length direction of the conjugated fiber in a direction approximately parallel to the surface of the nonwoven fabric with a high-temperature water vapor is approximately uniform in the thickness direction of the nonwoven fabric. Specifically, in each area of three areas obtained by dividing a cross section equally into three in a direction perpendicular to the thickness direction, particularly, in a middle area (inner layer), the number of the fibers forming a coil-like crimp having at least one turn is, for example, 5 to 50 pieces per area of 5 mm (in a length along with the surface direction) by 0.2 mm (in a length along with the thickness direction), preferably 10 to 50 pieces per area of 5 mm (in a length along with the surface direction) by 0.2 mm (in a length along with the thickness direction), and more preferably 20 to 50 pieces per area of 5 mm (in a length along with the surface direction) by 0.2 mm (in a length along with the thickness direction). In the nonwoven fabric of the present invention, owing to most of the crimped fiber long axes, which are parallel to the nonwoven fabric surface, the number of crimps is uniformly distributed in the thickness direction. Such a nonwoven fabric has a high stretchability without containing a rubber or an elastomer. In addition, the nonwoven fabric has a strength enough for practical use without an adhesive agent. Incidentally, the term "an area obtained by dividing the cross section into three with respect to the thickness direction" in the present description means each area of the three areas obtained by dividing the cross section with respect to the thickness direction of the nonwoven fabric equally into three in a direction perpendicular to the thickness direction.

In addition, the uniform distribution of the crimps in the thickness direction of the nonwoven fabric of the present invention is also evaluated from the uniformity of the curved ratio of fiber in the thickness direction of the nonwoven fabric. The curved ratio of fiber means a ratio ($L2/L1$) of a fiber length ($L2$) of the crimped fiber relative to a length between the both ends of the crimped fiber ($L1$). The curved ratio of fiber (particularly, the curved ratio of fiber in the middle area in the thickness direction of the nonwoven fabric) is, for example, not less than 1.3 (e.g., about 1.35 to 5), preferably about 1.4 to 4 (e.g., about 1.5 to 3.5), and more preferably about 1.6 to 3 (particularly, about 1.8 to 2.5). Incidentally, in the present invention, as described later, since the curved ratio of fiber is measured based on an electron micrograph of the cross section of the nonwoven fabric, the fiber length ($L2$) means not a fiber length obtained by straightening a fiber which is three-dimensionally crimped to measure the length (an actual length), but a fiber length obtained by straighten a fiber whose crimps are two-dimensionally observed on an electron micrograph (a fiber length on a photograph). That is, the fiber length of the present invention (the fiber length on the photograph) is shorter than the actual length.

Moreover, in the present invention, since the crimps are almost uniformly distributed in the thickness direction of the nonwoven fabric, the curved ratio of fiber is uniform in the thickness direction. The uniformity of the curved ratio of fiber in the present invention is evaluated by comparing the curved ratio of fiber of each area of the three areas obtained by dividing the cross section with respect to the thickness direction equally into three. That is, the curved ratio of fiber of any area of the three areas obtained by dividing the cross section with respect to the thickness direction equally into three is within the range mentioned above. The proportion of the minimum curved ratio of fiber relative to the maximum curved ratio of fiber in each area (the ratio of the minimum curved ratio of fiber among the three areas relative to the maximum curved ratio of fiber among the three areas) is, for example, not less than 75% (e.g., about 75 to 100%), preferably about 80 to 99%, and more preferably about 82 to 98% (particularly about 85 to 97%).

Specifically, the curved ratio of fiber and the uniformity of the curved ratio of fiber are measured as follows; (1) taking an electron micrograph of the cross section with respect to the thickness direction of the nonwoven fabric; (2) dividing the cross section on the photograph equally into three in a direction perpendicular to the thickness direction to obtain three areas [a surface layer (a surface area), an inner layer (a middle area), and a backside layer (a backside area)], each of which has the same thickness in the middle of the layer and is parallel to another in the thickness direction; (3) selecting a measuring area by adjusting the length of the measuring area to not less than 2 mm in the length direction of the nonwoven fabric and the width of the measuring area to an appropriate length to count the number of the fiber pieces suitable for measuring the curved ratio of fiber of not less than 100 pieces (preferably not less than 300 pieces, and more preferably about 500 to 1000 pieces); (4) measuring the curved ratio of fiber of all fibers in the measuring area of each area and calculating the average curved ratio of fiber of each area; and (5) comparing the average of the maximum curved ratio of fiber and the average of the minimum curved ratio of fiber among the three areas to calculate the uniformity of the curved ratio of fiber.

The potential crimping fiber constituting the nonwoven fabric has an approximately coil-like form after the crimp development, as mentioned above. The average curvature radius of the crimp or loop of the coil-like crimped fiber is selected from, for example, about 10 to 250 μm. The average curvature radius thereof is, for example, about 20 to 200 μm (e.g., about 50 to 200 μm), preferably about 50 to 160 μm (e.g., about 60 to 150 μm), and more preferably about 70 to 130 μm. Here, the average curvature radius is an index representing the average size of the loop of the coil-like crimped fiber. A large average curvature radius of the coil-like crimped fiber means that the crimped fiber has a loosely twisted coil-like form. In other words, the crimped fiber has a coil-like form having a small number of crimps or loops. Moreover, a small number of crimps provide a modest fiber entanglement, which is disadvantageous to producing a nonwoven fabric having a sufficient stretchability. On the other hand, the development of crimps having an excessively small average curvature radius provides an insufficient fiber entanglement, which reduces the strength of the web. In addition, it is difficult to produce a potential crimping fiber to develop such a crimp.

The average pitch between the crimps of the coil-like crimped conjugated fiber is, for example, about 0.03 to 0.5 mm, preferably about 0.03 to 0.3 mm, and more preferably about 0.05 to 0.2 mm.

The nonwoven fabric (fiber web) may further comprise other fibers (non-conjugated fibers) in addition to the conjugated fiber. The non-conjugated fiber may include, for example, a cellulose-series fiber [e.g., a natural fiber (e.g., a cotton, a wool, a silk, and a hemp or linen), a semisynthetic fiber (e.g., an acetate fiber such as a triacetate fiber), and a regenerated fiber (for example, a rayon, a polynosic, a cupra, and a lyocell (e.g., the registered trademark: "Tensel"))], in addition to a fiber comprising the above-mentioned non thermal adhesive resin under moisture or the above-mentioned thermal adhesive resin under moisture. The average fineness and average fiber length of the non-conjugated fiber are the same as those of the conjugated fiber. These non-conjugated fibers may be used alone or in combination. Among these non-conjugated fibers, the preferred one includes, for example, a regenerated fiber such as a rayon, a semisynthetic fiber such as acetate, a polyolefinic fiber such as a polypropylene or polyethylene fiber, a polyester fiber, and a polyamide fiber. In particular, in terms of blending fibers, the preferred one may be a fiber which is the same kind of the conjugated fiber. For Example, when the conjugated fiber is a polyester-series fiber, the non-conjugated fiber may also be a polyester-series fiber.

The proportion (mass ratio) of the conjugated fiber relative to the non-conjugated fiber [the conjugated fiber/the non-conjugated fiber] is, for example, about 80/20 to 100/0 (e.g., about 80/20 to 99/1), preferably about 90/10 to 100/0, and more preferably about 95/5 to 100/0. Blending the non-conjugated fiber with the conjugated fiber can balance between the strength with the tearability by hand of the nonwoven fabric. However, an excessively small amount of the conjugated fiber (potential crimping fiber) fails to provide recovery stress since the non-conjugated fiber hinders the crimped fiber from expanding and contracting, particularly, from contracting after the nonwoven fabric is elongated (or expanded).

The nonwoven fabric (fiber web) may further comprise a conventional additive, for example, a stabilizer (e.g., a heat stabilizer such as a copper compound, an ultraviolet ray absorber, a light stabilizer, and an antioxidant), an antibacterial agent, a deodorant, a perfume, a colorant (e.g., a dye or pigment), a filler, an antistatic agent, a flame retardant, a plasticizer, a lubricant, and a crystallization rate retardant. These additives may be used alone or incombination. These additives may be applied on the surface of the fiber or may be contained in the fibers.

(Properties of Nonwoven Fabric)

Mainly because of the change in the form of the conjugated fiber into a coil-like form at the crimp development of the conjugated fiber, the nonwoven fabric of the present invention has a structure in which each crimped conjugated fiber is entangled with another to fasten or hook the fiber on another, substantially without being melt-bonded to another. The outer shape or form of the nonwoven fabric may be selected according to applications. The outer shape is usually a rectangular sheet form such as a tape-shaped or belt-shaped form.

It is desirable for the nonwoven fabric of the present invention that most (or a large amount) of the fibers constituting the nonwoven fabric (or the long axis direction of the coil-like crimped fiber) be arranged in a direction approximately parallel to the nonwoven fabric surface (or sheet surface). Incidentally, the term "being arranged in a direction approximately parallel to the surface direction" means, for example, a state of the fibers in the nonwoven fabric which is free from the high frequent distribution of a large amount of the fibers (or the long axis direction of the coil-like crimped fiber) arranged in a direction parallel to the thickness direction of the nonwoven fabric, unlike a state of the fibers entangled with each other by needle punching.

The nonwoven fabric of the present invention comprises the conjugated fibers arranged in a direction parallel to the nonwoven fabric surface (the length direction) and crimped in a coil-like form (or helically crimped). In such a nonwoven fabric, the conjugated fibers adjacent to or intersecting with each other are entangled with each other by virtue of the helical crimps of the fibers. The entanglement of the crimped fibers occurs in a direction parallel to the surface of the nonwoven fabric. In the thickness direction (or an oblique direction) of the nonwoven fabric, the conjugated fibers are also entangled with each other. However, the entanglement of the fibers in the thickness direction (or an oblique direction) of the nonwoven fabric is loose. In particular, in the present invention, during the shrinkage or contraction of the conjugated fibers in the fiber web, i.e., during the change in the form of the conjugated fiber into a coil-like form, the helical crimps or loops of the conjugated fibers are entangled with another. Owing to the helical crimps or loops entangled with each other as mentioned above, the fibers are prevented from falling apart even when the nonwoven fiber is stretched. Therefore, the nonwoven fabric of the present invention can greatly be stretched in the surface direction (longitudinal direction) of the nonwoven fabric rather than in the width direction or in the thickness direction thereof. In addition, since the helical crimps forming the nonwoven fabric surface or protruding from the inside of the nonwoven fabric are easily entangled with each other by pressing the nonwoven fabric surfaces in contact against each other, the nonwoven fabric shows self-fastenability. Moreover, the entanglement of the helical crimps arranged in the surface and length directions are unraveled when the helical crimps are stretched or elongated by applying a tensile strength on the nonwoven fabric in the length direction thereof. Therefore, the nonwoven fabric is easy to tear. Accordingly, the nonwoven fabric of the present invention has stretchablity, tearability by hand, and self-fastenability in a well-balanced way.

However, the existence of a large amount of the fibers arranged in the thickness direction (a direction perpendicular to the sheet surface) of the nonwoven fabric, which are substantially not melt-bonded, produces a more intricate entanglement of the fibers at the crimp development. In such a case, the moves of the crimped fibers are so greatly restrained that the helical crimps are prevented from expanding and shrinking (or contracting), thereby providing a nonwoven fabric having a low stretchability. For that reason, it is desirable that the fibers be arranged in a direction as parallel as possible to the sheet surface.

Since the coil-like crimped fibers of the nonwoven fabric of the present invention are arranged in a direction approximately parallel to the surface direction, as mentioned above, the nonwoven fabric has stretchability in the surface direction. On the other hand, when the nonwoven fabric is stretched in the thickness direction, the crimped fibers entangled with each other are easily raveled out. Therefore, when the nonwoven fabric is stretched in the thickness direction, the nonwoven fabric does not show such stretchability as a stretchability (contracting or shrinking property) which is observed at an elongation in the surface direction. Incidentally, even though the fibers are so compactly arranged that the visual observation of the fiber arrangement is difficult, the degree of fiber arrangement is determined easily based on the observation of the stretchability mentioned above.

The density (bulk density) of the nonwoven fabric can be selected from, for example, the range of about 0.01 to 0.5 g/cm$^3$. The density thereof may be, for example, about 0.03 to 0.3 g/cm$^3$, preferably about 0.05 to 0.3 g/cm$^3$, and more preferably about 0.06 to 0.2 g/cm$^3$ (particularly about 0.07 to 0.15 g/cm$^3$).

The nonwoven fabric of the present invention preferably has a plurality of low-density portions (regions) and a plurality of high-density portions (regions). It is preferred that the low-density portion and high-density portion are alternately formed in the surface direction (or in the longitudinal direction) in a periodical pattern. Owing to the density difference which may be produced in a specific period or pattern, the nonwoven fabric of the present invention can have stretchability as well as tearability by hand. The structure (or pattern) of the low-density portion and the high-density portion is not particularly limited to a specific one as long as the low-density portion and the high-density portion are alternately formed in a periodic pattern. A pattern for a tape- or belt-shaped nonwoven fabric may be a striped pattern having the low-density portion and the high-density portion alternately formed in the length direction of the nonwoven fabric. The preferred one for the tape- or belt-shaped nonwoven fabric has the low-density portion and the high-density portion alternately formed in a mesh pattern or in a cross-striped pattern (hound's-tooth check pattern) in the length direction of the nonwoven fabric. The areas of the low-density and high-density portions of the mesh pattern or cross-striped pattern structure may not necessarily be equal. For example, the area ratio (%) of the low-density portion relative to the high-density portion [the low-density portion/the high-density portion] can be selected from, for example, about 90/10 to 10/90 and preferably about 70/30 to 30/70 or may be almost 1. The average width of each portion is, for example, about 0.1 to 10 mm, preferably about 0.5 to 5 mm, and more preferably about 1 to 3 mm.

The basic weight of the nonwoven fabric (fiber web) before heating is, for example, about 10 to 200 g/m$^2$ and preferably about 20 to 100 g/m$^2$. An excessively small basic weight does not provide sufficient physical properties. On the other hand, an excessively large basic weight sometimes prevents crimps from being developed uniformly.

The basic weight of the nonwoven fabric of the present invention (the nonwoven fabric after heating) can be selected from, for example, the range of about 10 to 300 g/m$^2$, preferably about 20 to 250 g/m$^2$, and more preferably about 30 to 200 g/m$^2$. The thickness of the nonwoven fabric can be selected from, for example, the range of about 0.1 to 10 mm. The thickness thereof is, for example, about 0.2 to 5 mm, preferably about 0.3 to 3 mm, and more preferably about 0.4 to 1.5 mm. The nonwoven fabric having a basic weight or thickness within the range mentioned above has stretchability and tearability in a well-balanced way.

The elongation at break in at least one direction (e.g., a length direction of a tape-shaped nonwoven fabric) of the nonwoven fabric of the present invention may be not less than 50%, preferably not less than 60% (e.g., about 60 to 300%), and more preferably not less than 80% (e.g., about 80 to 250%). The nonwoven fabric having an elongation at break within the range mentioned above has a high stretchability.

The recovery of the nonwoven fabric of the present invention after being subjected to 50% elongation in at least one direction (the recovery after 50% elongation) may be not less than 70% (e.g., 70 to 100%), for example, not less than 80% (e.g., 80 to 100%), preferably not less than 90% (e.g., 90 to 100%), and more preferably not less than 95% (e.g., 95 to 100%). The nonwoven fabric having a recovery after elongation within the range mentioned above has a high conformability to move of the nonwoven fabric being elongated. For example, the nonwoven fabric used as a bandage conforms to the form of a part to which the nonwoven fabric is applied, and the nonwoven fabric surfaces in contact are pressed against each other to immobilize and compress the part properly. In particular, when the nonwoven fabric is wound twice or more by overlapping the surfaces thereof, fastening force is produced by pressing the nonwoven fabric surfaces in contact against each other. The generated fastening force consequently corresponds to an entire recovery stress. The entire recovery stress mentioned above is similar to a recovery stress of a nonwoven fabric having an increased basic weight. That is, when a nonwoven fabric having a small recovery after elongation is used for winding around a body part having a complicate shape or when a body part which is being wrapped with a nonwoven fabric having a small recovery after elongation accidentally moves, the nonwoven fabric cannot conform to the shape or move and the deformation of the nonwoven fabric due to the movement is not restored. In such a case, the immobilization of the nonwoven fabric wrapped around part becomes deteriorated.

The nonwoven fabric of the present invention shows behavior in recovery after 50% elongation in at least one direction. The stress at 25% elongation in 50% elongation in at least one direction [elongation stress (X)] and the stress at 25% elongation in recovery after 50% elongation [recovery stress (Y)] are measured. The ratio of the recovery stress (Y) relative to the elongation stress (X) [(Y/X)] may be not less than 0.05, for example, not less than 0.1, preferably not less than 0.3, and more preferably not less than 0.4 (particularly, about 0.5 to 1.0). A nonwoven fabric having a high ratio of the recovery stress (Y) relative to the elongation stress (X) can maintain a high stress at recovery after being elongated. When such a nonwoven fabric is used as a tape to wind around a body part, the body part is more firmly immobilized. A nonwoven fabric having a small ratio of the recovery stress (Y) relative to the elongation stress (X) has a low stress at recovery. That is, when such a nonwoven fabric is used as a tape to wind around a body part, the immobilizing property of the tape is low. Accordingly, the nonwoven fabric mentioned above is not suitable for an application such as a bandage.

The nonwoven fabric of the present invention has also an excellent self-fastenability and is suitable for using as a tape such as a bandage. Incidentally, the self-fastenability is a property or an ability to fasten itself or hook onto itself by bringing the surfaces into contact to couple or entangle the surfaces in contact with each other without using an adhesive agent or the like. Specifically, after the nonwoven fabric as a bandage is wound around an object once, an end of the bandage is overlapped in place on the underlying nonwoven fabric (or the bandage is torn and the end produced or formed by tearing is overlapped) and fastened. In a series of the actions mentioned above, with being elongated, the nonwoven fabric surfaces in contact are pressed against each other to join or to couple the surfaces in contact with each other, whereby the nonwoven fabric shows self-fastenability. In this case, ideally, the nonwoven fabric surfaces in contact are joined or coupled with a strength higher than the breaking strength of the nonwoven fabric. In practice, the way or direction of winding the nonwoven fabric around an objective part often depends on the state or shape of the part. Changing the way or direction of winding the nonwoven fabric increases the frictional force of the nonwoven fabric surfaces in contact, which increases the self-fastenability of the nonwoven fabric. Therefore, even though the strength between the surfaces in contact is lower than the strength at break, the bandage can practically be fastened. The strength between the nonwoven fabric surfaces in contact is difficult to measure. To overcome the difficulty, in the present invention, "slip stress at curved surfaces in contact" is used for evaluation of the self-fastenability (slip resistance at curved surfaces in contact). The nonwoven fabric which can be used as a bandage in practice preferably requires a predetermined self-fastenability and a "slip stress at curved surfaces in contact" of not less than 0.5N/50 mm, and more preferably not less than 1.0N/50 mm (particularly not less than 3.0 N/50 mm). The stress at curved surfaces in contact plays an important role in the self-fastenability of the nonwoven fabric. The larger the slip stress at curved surfaces in contact is, more firmly the nonwoven fabric can be fastened after winding the nonwoven fabric around an objective part and tearing the nonwoven fabric. Accordingly, an excessively small slip stress at curved surfaces in contact fails to fasten the nonwoven fabric firmly, whereby the nonwoven fabric wound around the part gradually unfastens from the end of the nonwoven fabric. Incidentally, using a tensile tester, the slip stress at curved surfaces in contact is measured in accordance with the method set forth in Examples described later.

Moreover, a large number of the coil-like crimped fiber or crimped fiber having a loop protruding from the inside of the nonwoven fabric or forming the nonwoven fabric surface improves the fastenability due to the entanglement of the crimped fibers of the nonwoven fabric surfaces in contact. In addition, a bandage end produced or formed by tearing after winding the nonwoven fabric around an objective matter (e.g., a body part such as a hand or a finger) has the crimped fibers freely moving (the free fibers which are sticking out of the end or which have an fiber end formed by tearing). The free fibers can freely be entangled with the coil-like crimped fibers or crimped fibers having a loop of the underlying nonwoven fabric, whereby a highly excellent self-fastenability is provided. The number of the coil-like crimped fibers or crimped fiber having a loop of the nonwoven fabric surface is, for example, not less than 7 pieces per 1 $cm^2$, preferably about 8 to 50 pieces per 1 $cm^2$, and more preferably about 9 to 45 pieces per 1 $cm^2$ (particularly about 10 to 40 pieces per 1 $cm^2$). Incidentally, in the present invention, the concrete measuring method of the number of the coil-like crimped fibers or crimped fibers having a loop is the method described in Examples.

Furthermore, the strength at break of the nonwoven fabric of the present invention is, for example, about 5 to 30 N/50 mm, preferably about 6 to 25 N/50 mm, and more preferably about 7 to 20 N/50 mm in at least one direction (e.g., a length direction). The strength at break plays an important role in the tearability by hand. The feature of the nonwoven fabric of the present invention is easy to tear by hand. The nonwoven fabric to be used as a bandage also requires "tenacity" against tearing. The "tenacity" means that even though the nonwoven fabric gets a cut which triggers tearing in its use, the nonwoven fabric does not easily tear from the cut. That is, since the break of the nonwoven fabric is easily triggered as tearing starts, the tearability by hand of the nonwoven fabric could ultimately depend on the strength at break. Accordingly, an excessively large strength at break makes it difficult to tear the nonwoven fabric by one hand in its use. On the other hand, a nonwoven fabric having an excessively small strength at break lacks strength and breaks easily. Such a nonwoven fabric is not easy to use.

In particular, the nonwoven fabric to be used as a bandage requires a certain strength to fasten the end formed by tearing the bandage after winding the bandage around an affected part or the like as much as need, being stretched in the length direction. Therefore, it is preferable that the strength at break of the nonwoven fabric satisfy the above mentioned range in the length direction of the bandage.

In addition, in order to produce a bandage from the nonwoven fabric of the present invention, it is necessary to process the nonwoven fabric to give a desirable width or length of the bandage. The above-mentioned process is usually facilitated using a slitter rewinder. Accordingly, in the present invention, in order to secure an efficient production of the bandage it is also preferable that the strength at break of the nonwoven fabric be within the above-mentioned range in the length direction.

On the other hand, the strength at break in the width direction may be lower than the strength at break in the longitudinal (lengthwise) direction. The strength at break in the width direction may be, for example, about 0.05 to 20 N/50 mm, preferably about 0.1 to 15 N/50 mm, and more preferably about 0.5 to 10 N/50 mm (particularly about 1 to 8 N/50 mm).

As mentioned above, the nonwoven fabric of the present invention is not only anisotropic in the surface direction and the thickness direction but also usually anisotropic in the machine direction (MD) and the cross direction (CD). That is, in the production process for the nonwoven fabric of the present invention, the axis directions of the coil-like crimped fibers tend to be arranged not only in a direction approximately parallel to the surface direction of the nonwoven fabric but also in a direction approximately parallel to the machine direction. As a result, a nonwoven fabric produced in rectangular form has stretchabilities and properties at break, each being different in the machine direction and the cross direction. In particular, the nonwoven fabric has strengths at break different in the machine direction and the cross direction. In order to use such a nonwoven fabric as a bandage, the machine direction of the nonwoven fabric is allowed to correspond to the length direction of the nonwoven fabric to impart a strength at break within the range mentioned above to the nonwoven fabric. Concretely, the strength at break in the length direction (machine direction) relative to that in the cross direction is, for example, about 1.5 to 50, preferably about 2 to 40, and more preferably about 3 to 30. In addition, letting the strength at break in the length direction be 1, the strength at the cross direction is, for example, about 0.01 to 1, preferably about 0.03 to 0.8, and more preferably about 0.05 to 0.6 (particularly about 0.1 to 0.5).

The nonwoven fabric of the present invention preferably has water repellency. This is the reason why the use of nonwoven fabric for applications where the fabric contacts with a human body, particularly, such as a bandage or a supporter, prevents water on the outer layer of the nonwoven fabric wrapped around an affected area from getting therethrough and reaching the affected area. The water repellency is imparted to the nonwoven fabric to be treated with water or a water vapor (or untreated nonwoven fabric). In the production process described later, the fibers of the untreated nonwoven fabric is exposed to water or a water vapor to wash away a hydrophilic material adhered to the fibers, whereby the fibers are allowed to exhibit the inherent behaviors of the resin on the surface of the fibers. The concrete water repellency preferably shows a score of not less than 3 (preferably 3 to 5, and more preferably 4 to 5) in JIS L1092 Testing methods for water resistance of textiles (Spray test).

In addition, the washing-away action with water or a water vapor removes an oil for a fiber which has been adhered to the fibers as well, leading to a decrease in skin irritation of the nonwoven fabric of the present invention.

The nonwoven fabric has an air-permeability of not less than 0.1 $cm^3/cm^2 \cdot second$ measured in accordance a Fragzier tester method, for example, about 1 to 500 $cm^3/cm^2 \cdot second$, preferably about 5 to 300 $cm^3/cm^2 \cdot second$, and more preferably about 10 to 200 $cm^3/cm^2 \cdot second$. Since the nonwoven fabric of the present invention also has a high air-permeability, the nonwoven fabric is suitable for applications for a human body such as a bandage.

[Production Process of Nonwoven Fabric]

The production process of the nonwoven fabric of the present invention comprises a step for forming a fiber web with the fibers comprising the conjugated fiber and a step for heating the conjugated fiber web to develop a crimp.

Firstly, in the step for forming a web from the fiber, a web is formed with the fiber comprising the conjugated fibers. The web-forming process which may be used includes a conventional process, e.g., a direct process such as a spun bond process or a melt-blow process, a carding process using a melt-blow fiber or a staple fiber, and a dry process such as air-laid process. Among these processes, a carding process using a melt-blow fiber or a staple fiber, particularly, a carding process using a staple fiber is commonly used. The web obtained by using the staple fiber may include, e.g., a random web, a semi-random web, a parallel web, and a cross-wrap web.

The obtained fiber web is then subjected to a step for heating the web to crimp the fibers thereof in order to produce a nonwoven fabric. In the obtained nonwoven fabric, the conjugated fibers are arranged with putting the fiber length direction to a direction parallel to the web surface, and the crimps having a specific curvature radius are distributed almost uniformly in the thickness direction of the nonwoven fabric. However, in the present invention, in order to prevent the potential crimping fibers from scattering in the step for heating the web to crimp the potential crimping fibers, a step for entangling the fibers in an area of the fiber web loosely with each other is preferably performed before the step for heating the web. The fiber-entangling step mentioned above may be a process for entangling the fibers mechanically. The preferred one includes a process for entangling the fibers by applying or spraying (or ejecting) a low-pressure water to the web. The process comprising the step spraying a low-pressure water, in the present invention, is not a process for entangling the fibers firmly using a water flow to produce a high web strength (e.g., a common hydroentangled nonwoven fabric), but a process for restraining the move of the fibers by bringing the fiber web in a wet state to fix the fibers loosely. In such an entangling process using a low-pressure water, the spray of water may be continuously, preferably, intermittently or periodically. The intermittent or periodic spray of a low-pressure water to the fiber web forms a plurality of low-density portions and a plurality of high-density portions. The low-density portion and the high-density portion are formed alternately in a periodic pattern. Owing to the formation of density difference in the fiber web, the fibers in an area of the fiber web, mainly in the high-density portion, are loosely entangled with each other to prevent the fiber from scattering by spraying with a high-temperature and high-pressure water vapor in the next step. On the other hand, in the low-density portion, the fiber entanglement hardly occurs since the amount of the fibers is small. In addition, less fiber-fiber contacts do not prevent the fibers from moving freely, which is advantageous to an excellent crimp development.

That is, the water ejection pressure in the step for entangling the fibers is preferably as low as possible in order to entangle the fibers loosely with each other. The water ejection pressure is, for example, about 0.1 to 1.5 MPa, preferably about 0.3 to 1.2 MPa, and more preferably about 0.6 to 1.0 MPa. Incidentally, the water temperature is, for example, about 5 to 50° C., preferably about 10 to 40° C., for example, about 15 to 35° C. (a room temperature).

The process for spraying the web with water intermittently or periodically is not particularly limited to a specific one as long as the process can produce the density differences (i.e., the high-density and low-density portions) are alternately formed in a periodic pattern. The preferred one includes a process for ejecting water to the fiber web through a plate-like matter (e.g., a porous plate) having a plurality of pores forming a spraying area or pattern in a regular form in terms of the convenience.

Concretely, the fiber web obtained in the step for forming a fiber web is transferred by a belt conveyor to the next step. Then the fiber web may be transferred to pass through a clearance between a drum comprising a porous plate (a porous plate drum) and the conveyor belt, being placed on the conveyor belt. The conveyor belt may be water-permeable. The use of such a conveyor belt allows a water mist ejected from the porous plate drum inside at a pressure within the range mentioned above to penetrate the fiber web and the conveyor belt while the fiber web is passing through the clearance between the porous plate drum and the belt. The water sprayed in this manner moves aside the fibers constituting the web on the belt to a non-sprayed area which is not corresponding to a pore of the porous plate, whereby the amount of the fiber in the area corresponding to the pores is reduced. In this stage, the density difference may be produced by spraying the web with water to form pores in the areas corresponding to the pores of the drum (sprayed areas).

The pore alignment or arrangement structure of the porous plate is not particularly limited to a specific one. The pore alignment structure may be, for example, a pore alignment structure in which the pores are disposed in a mesh pattern or cross-striped pattern (hound's-tooth check pattern). Each pore usually has the same size. The size is, for example, about 1 to 10 mm, preferably about 1.5 to 5 mm. The pitch between the pores adjacent to each other is usually the same. The pitch therebetweeen is, for example, about 1 to 5 mm, preferably about 1.5 to 3 mm.

An excessively small pore size decreases the amount of the water passing through the pores, whereby the fibers of the fiber web are sometimes not moved aside by the water passing through the web. An excessively large pore size requires widening the pitch between the pores, in order to stabilize a form of a drum. The use of such a drum often produces or forms an area which is not contacted with water in the web, whereby an irregularity of quality is caused or a uniform treatment of the web becomes difficult. In addition, an excessively small pitch between the pores requires reducing the pore size, and the amount of the water is reduced. The use of a drum having an excessively large pitch between the pores produces or forms an area which is not contacted with water as well, whereby an irregularity of quality is caused.

Finally, the fiber web in which the fibers loosely entangled with each other in places is transferred by the belt conveyor for the next step. In the step, the web comprising the potential crimping fibers is heated to crimp the fiber. The heating process may be a dry heat treatment. The preferred one includes a treatment with a high-temperature water vapor. In the high-temperature water vapor treatment, the fiber web transferred by the belt conveyor is exposed to a high-temperature or a heated water vapor (high pressure steam) flow to crimp the conjugated fibers (potential crimping fibers), whereby the nonwoven fabric of the present invention is obtained. That is, in the present invention, during the crimp development, the conjugated fibers shrink or the form of the fibers changes into a coil-like form to entangle the fibers three-dimensionally.

In a common production step of a nonwoven fabric comprising the conjugated fibers, a step for fixing the fibers (fiber-entangling step) and a heating step for developing crimps of the potential crimping fibers are separately performed. Therefore, it is necessary that a fiber web comprising the conjugated fiber as a main component be subjected to fiber-entangling step by a needle-punching or hydroentangling to provide the web with a form suitable or stable for processing in the next step and then the web be subjected to a dry heating treatment to crimp the fibers. For that reason, the nonwoven fabric obtained by the conventional production process has strongly entangled fibers after the heat treatment, thereby increasing stress at elongation in the length direction. Such a nonwoven fabric is difficult to tear by hand with ease. In the present invention, the fiber web having a fiber entanglement as minimized as possible is subjected to heat (particularly, a high-temperature water vapor treatment) to develop the crimps of the fibers and to entangle the fibers at the same time, whereby easy-tearability is attained.

Concretely, the fiber web treated with a water at a low pressure is subjected to a high-temperature water vapor treatment, being transferred by the belt conveyor. As soon as the high-temperature water vapor treatment starts, the fiber web contracts or shrinks. Accordingly, it is preferable that an excess amount of the fiber web be fed just before being exposed to a high-temperature water vapor. Depending on an objective size of the nonwoven fabric, the web is overfed at a rate of about 110 to 300%, and preferably about 120 to 250% per objective length of the nonwoven fabric.

The belt conveyor to be used is not particularly limited to a specific one as long as the conveyor can principally transfer the fiber web without deforming the form of the fiber web. The preferably used one includes an endless conveyor. Incidentally, a common single belt conveyer may be used, and according to need, a combination of the common single belt conveyers (i.e., two common single belt conveyers) may be used to transfer the fiber web with holding the web between the belts of these conveyors. Transferring the web by the two conveyers in the above-mentioned manner prevents the deformation of the web being transferred due to an external force such a high-temperature water vapor (steam) or a vibration of the conveyer at the web treatment.

In order to supply the fiber web with a water vapor, a conventional water vapor spraying apparatus is used. The preferred one includes an apparatus which can spray the fiber web approximately uniformly in the entire width direction with a water vapor at a desirable pressure and amount. In the combination use of the two belt conveyors, a first conveyor may have a first vapor spraying apparatus for supplying the web with the vapor disposed therebehind to supply the web with the vapor through a water-permeable conveyor belt or the conveyor net placed on the conveyor, and a second conveyor may have a first suction box disposed therebehind. A surplus vapor which has passed through the web may be removed by the suction box. However, in order to apply the water vapor on the fiber web sufficiently and to develop the crimps of the fiber due to the heat of the water vapor more efficiently, it is necessary to prevent the web from being applied a force as much as possible. Therefore, it is preferable that the water vapor be supplied without suction by the suction box. In addition, in order to treat the both surfaces of the web with the vapor at once, the first conveyer may further have a second suction box disposed behind the conveying surface, being distanced from the first vapor spraying apparatus in the traveling direction of the web, and the second conveyer may further has a second vapor spraying apparatus disposed behind the conveying surface. An alternative process for subjecting the both surfaces of the fiber web to the vapor treatment without the second vapor spraying apparatus is as follows: allowing the fiber web to pass through the clearance between the first vapor spraying apparatus; reversing the obtained fiber web; and allowing the reversed fiber web to pass through therebetween to subject another surface of the web to the vapor treatment.

The endless belt to be used for the conveyer is not particularly limited to a specific one as long as the belt does not hinder the transport of the web or the high-temperature vapor treatment. When a net is used as an endless belt, a net having a mesh count smaller than about 90 (e.g., about 10 to 50) is preferred. A net having a mesh count more then above-mentioned number has a low air-permeability and makes it difficult to allow the water vapor to pass therethrough. The preferred material of the belt in terms of heat resistance for the water vapor treatment or the like includes, for example, a metal, a polyester-series resin treated for heat resistance, and a heat-resistant resin such as a polyphenylenesulfide-series resin, a polyarylate-series resin (a fully aromatic-series polyester-series resin) or an aromatic polyamide-series resin.

The high-temperature water vapor sprayed from the water vapor spraying apparatus is an air (or gaseous) flow and enters the inside of the web being treated without moving the fibers thereof greatly, unlike a hydroentangling or a needle-punching. Presumably, this water vapor-entering effect allows the vapor to cover the surface of each fiber of the web efficiently, whereby the uniform crimp development due to heat can be attained. Moreover, since the water vapor treatment can transmit or conduct heat to the inside of the fiber more sufficiently than a dry heat treatment, the degree of crimping is almost uniform in the surface direction and the thickness direction of the nonwoven fabric.

For spraying the high-temperature water vapor, a plate or die having a plurality of predetermined orifices arranged continuously in a width direction thereof is used as a nozzle, and the plate or die is disposed to arrange the orifices in the width direction of the fiber web to be conveyed. The plate or die may have at least one orifice line or a plurality of orifice lines, being parallel to each other. Moreover, it is possible that a plurality of nozzle dies, each having one orifice line, be disposed being parallel to each other.

The thickness of a plate nozzle having an orifices formed thereon may be about 0.5 to 1 mm. The diameter of the orifice or the pitch between the orifices is not particularly limited to a specific one as long as the condition of the diameter or pitch thereof efficiently provides an objective crimp development and a fiber entanglement in the crimp development. The diameter of the orifice is usually, about 0.05 to 2 mm, preferably about 0.1 to 1 mm, and more preferably about 0.2 to 0.5 mm. The pitch between the orifices is, usually, about 0.5 to 3 mm, preferably about 1 to 2.5 mm, and more preferably about 1 to 1.5 mm. An excessively small diameter of the orifice tends to cause difficulties, for example, a difficulty in producing such a nozzle with a high accurate process and a difficulty in using such a nozzle due to a frequent plugging of the orifice. An excessively large diameter of the orifice decreases the power for jetting with vapor of the nozzle. On the other hand, an excessively small pitch between the orifices makes the distance between nozzle holes so close that the strength of the nozzle is decreased. An excessively large pitch between the orifices causes a possible insufficient contact of a high-temperature water vapor with the fiber web, whereby the strength of the obtained web is low.

The high-temperature water vapor to be used is not particularly limited to a specific one as long as an objective crimp development of the fibers and an appropriate fiber entanglement in the crimp development can be achieved. The pressure of the high-temperature water vapor is, according to the quality of material or form of the fiber to be used, for example, about 0.1 to 2 MPa, preferably about 0.2 to 1.5 MPa, and more preferably about 0.3 to 1 MPa. An excessively high or strong pressure of the water vapor disturbs the arrangement of the fibers constituting the web or entangles the fibers more than need. In addition, in an extreme case, the fibers are melt-bonded, whereby an objective stretchability is hardly achieved. On the other hand, an excessively weak pressure of the water vapor fails to give an amount of heat which is necessary to the crimp development of the fibers or allow a water vapor to penetrate the fiber web, whereby the distribution of the crimp of the fibers tends to be ununiform in the thickness direction of the nonwoven fabric. Moreover, controlling uniform ejection of the water vapor from the nozzle is difficult.

The temperature of the high-temperature water vapor is, for example, about 70 to 150° C., preferably about 80 to 120° C., and more preferably about 90 to 110° C. The speed of the treatment with the high-temperature water vapor is, for example, about not more than 200 m/minute, preferably about 0.1 to 100 m/minute, and more preferably about 1 to 50 m/minute.

Sometimes the nonwoven fabric has water remaining therein after the crimp development of the composite fibers of the fiber web. If necessary, the web after the water vapor treatment may be dried. It is necessary that the fibers of the surface of the nonwoven fabric be not bonded by the heat from a heating element for drying in contact with the nonwoven fabric and the nonwoven fabric do not deteriorate stretchability after drying. As long as the stretchability of the nonwoven fabric is maintained after the drying, the drying can employ a conventional manner (or process). For example, a large-scale dryer which is used for drying a nonwoven fabric, such as a cylinder dryer or a tenter dryer may be used. However, since the amount of the water remaining in the nonwoven fabric is so small that the nonwoven fabric can practically be dried by a relatively simple drying means, the drying preferably used is a non-contacting manner (e.g., an extreme infrared rays irradiation, a microwave irradiation, and an irradiation of electron beam) or a manner for spraying a hot air or a manner for allowing a hot air to pass through the nonwoven fabric.

The nonwoven fabric obtained by the above-mentioned manner is a nonwoven fabric which has been exposed to water and then a high-temperature water vapor atmosphere in the production process. That is, since the nonwoven fabric of the present invention is a nonwoven fabric which has been subjected to a treatment similar to a washing, an extraneous matter (such as spinning oil) has been washed away from the fiber. Accordingly, the nonwoven fabric of the present invention is sanitary and shows a high water repellency.

INDUSTRIAL APPLICABILITY

As mentioned above, since the nonwoven fabric of the present invention is stretchable and easily tearable by hand, the nonwoven fabric is suitable for various tapes and the like requiring flexibility and tearability. In particular, since the nonwoven fabric of the present invention has air-permeability and self-fastenability, being free from an adhesive agent, the nonwoven fabric is suitable for an application where the nonwoven fabric contacts with a human body, for example, a tape (e.g., a bandage and a supporter used for a medical application and a sport field).

EXAMPLES

Hereinafter, the following examples are intended to describe this invention in further detail and should by no means be interpreted as defining the scope of the invention. Incidentally, each physical property value in Examples was measured by the following method(s) or manner(s).

(1) Intrinsic Viscosity of Polyethylene Terephthalate Resin

One gram of a sample of a polyethylene terephthalate was dissolved in 0.1 L of a mixed solvent which contained phenolandtetrachloroethanein equal mass. The flow times of the mixed solvent and the obtained solution at 30° C. were mea sured using a viscometer. The intrinsic viscosity [η] was calculated from the following formula (1):

[Number 1]

$$\eta_{sp} = (t - t_0)/t_0 = (t/t_0) - 1 \quad (1)$$
$$[\eta] = \lim_{C \to 0} \eta_{sp}/C$$

providing that t is the flow time (second) of the obtained solution, to is the flow time (second) of the mixed solvent, and C is the concentration (g/L) of the sample.

(2) Number of Crimps

In accordance with JIS L1015 "Test methods for manmade staple fiber" (8.12.1), the number of crimps was evaluated.

(3) Average Curvature Radius

Using a scanning electron microscope (SEM), macrophotograph of a cross section of a nonwoven fabric was taken (100 magnifications). Among the fibers observed in the photograph of the nonwoven fabric cross section, the average curvature radius of a fiber which formed helix (coil) having a number of at least one turn was measured by the following method: drawing a circle along with a turn formed by the helix; observing the circle of the crimped fiber from the coil axis direction; and measuring a radius of the circle. Incidentally, in case of the fiber forming a spiral having an oval shape, let the half of the sum of the lengths of the major and minor axes of the oval-shaped loop or crimp be the curvature radius. Providing that only an oval having a ratio of the major axis relative to the minor axis within the range 0.8 to 1.2 was focused as a measuring object, a fiber forming an insufficient (deformed or odd) crimp or loop or a fiber forming a helix having a fake or false oval on the photograph was not included in the measuring object. The fake or false oval was a shape viewed as an oval form a direction deviating from the coil axis direction. Incidentally, the curvature radius was measured with respect to an SEM image of a cross section arbitrarily selected. The average curvature radius was calculated, given 100 as an n number.

(4) Basic Weight

In accordance with JIS L1913 "Test methods for nonwovens made of staple fibers", the basic weight was measured.

(5) Thickness and Density

In accordance with JIS L1913 "Test methods for nonwovens made of staple fibers", the thickness was measured. The density was calculated from the obtained thickness and the basic weight measured by the method in (4).

(6) Strength at Break and Elongation at Break

In accordance with JIS L1913 "Test methods for nonwovens made of staple fibers", the strength at break and elongation at break were measured. Incidentally, each of the strength at break and elongation at break was measured in machine direction (MD) and cross direction (CD).

(7) Water Repellency

In accordance with JIS L1092 "Testing methods for water resistance of textile" (6.2 Spray test), the water repellency was evaluated.

(8) Slip Stress at Curved Surfaces in Contact

The slip stress at curved surfaces in contact was measured by the following method.

Firstly, an object nonwoven fabric to be measured was cut to give a sample 1 having a width of 50 mm and a length of 600 mm, allowing the machine direction (MD) to correspond to the length direction of the sample 1. Next, as shown in FIG. 1 (1), an end of the sample 1 was fixed on a core pipe 3 (a pipe roll which was made of a polypropylene resin and had an outer diameter of 30 mm and a length of 150 mm) with a scotch tape 2, and using an alligator clip 4 (the gripping distance was 50 mm, and a rubber sheet having a thickness of 0.5 mm had been fixed on the inside of the clip with a double-faced adhesive tape before use), a 150 g-weight 5 was attached to another end of the sample 1 to apply the entire weight on the whole width of the sample 1 evenly.

Figure 2:
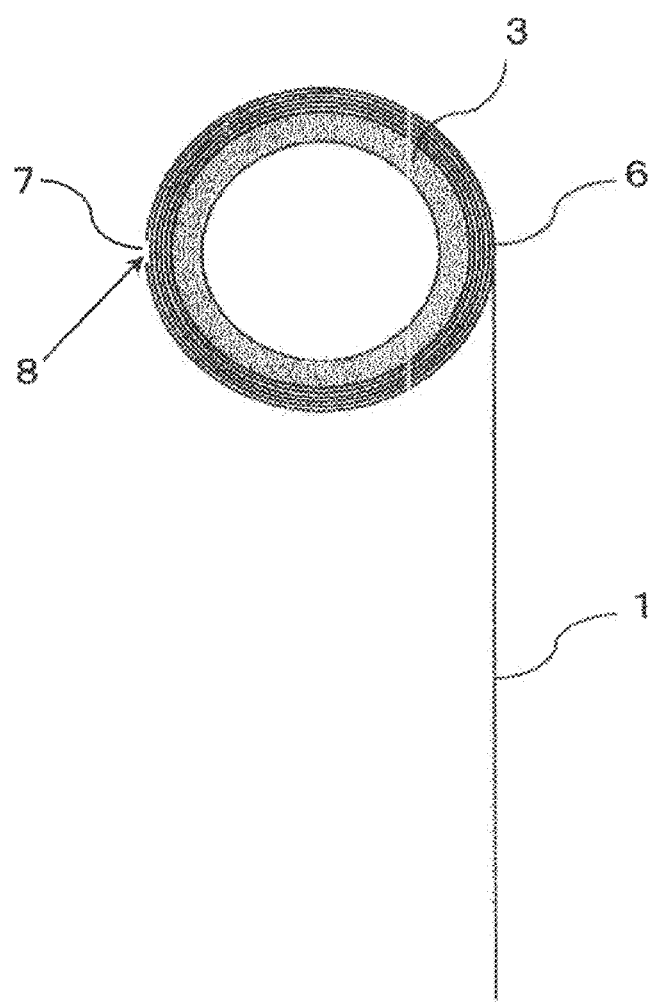
FIG. 2 is a schematic cross sectional diagram showing a sample to be used for determination of a slip stress at curved surfaces in contact in the present invention.

The core roll (pipe roll) 3 which was suspending the weight 5 through the sample 1 was rolled up and made five turns to lift the weight 5, paying attention to minimize the swing of the weight 5 (see FIG. 1 (2)). In this state of the sample 1 and the weight 5, let a boundary between an outermost layer of the sample 1 formed into a cylinder by winding the sample 1 around the pipe roll 3 and a plane area of the sample 1 unwound be a base point 6. The boundary was regarded as a border line between an area of the sample 1 wound around the pipe roll 3 and an area of the sample 1 straighten by the gravity of the weight 5. Keeping the state mentioned above, i.e., paying attention to keep the position of the base point 6, the alligator clip 4 and the weight 5 were quietly removed from the end of the sample 1. Then the sample 1 wound around the pipe roll 3 was cut at a point 7 which was located a half-circle away from the base point 6, with a razor, to give a cut 8, paying attention to avoid cutting the underlying sample 1 (see FIG. 2). Incidentally, the point 7 also corresponded to an imaginary point 6, which would be obtained if the pipe roll would be rotated by 180°.

Figure 3:
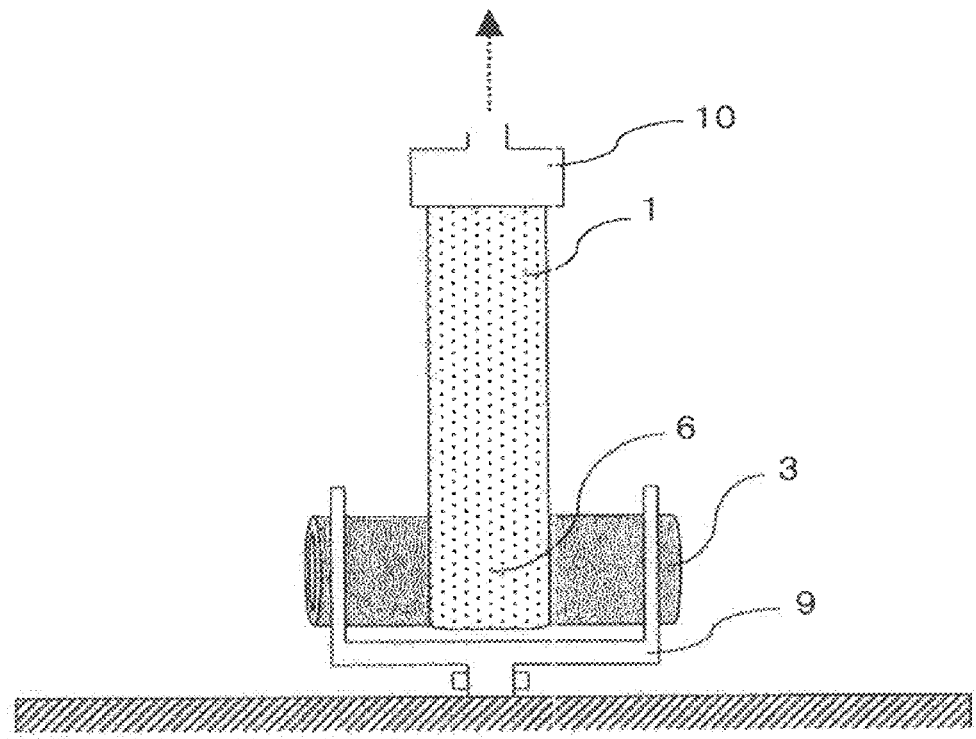
FIG. 3 is a schematic diagram showing a manner of determining of a slip stress at curved surfaces in contact in the present invention.

The slip stress at curved surfaces in contact of the sample 1, i.e., the slip stress at curved surfaces in contact between the outermost layer area and the inner layer area which had been placed under the outermost layer and wound around the pipe roll 3 was measured using a tensile tester ("Autograph" manufactured by Shimadzu Corporation). The pipe roll 3 was fixed on a jig 9 disposed on a chuck base at a fixed lateral stationary side of the tensile tester (see FIG. 3). The end of the sample 1 (the end to which the alligator clip 4 had been attached) was gripped by a chuck 10 at a load cell side to stretch the sample 1 at a tensile speed of 200 mm/minute. When the sample 1 was torn (separated) at the cut 8, the measured value (tensile strength) was regarded as the slip stress at curved surfaces in contact. Incidentally, when the sample 1 was broken before torn at the cut 8 because of the slip stress at curved surfaces in contact which was strong enough to surpass the strength at break, the sample 1 was evaluated as "broken".

(9) Recovery after 50% Elongation

In accordance with JIS L1096 "Testing method for woven fabrics", the recovery after 50% elongation was measured. Providing that the evaluation of the recovery in the present invention was uniformly based on an elongation of 50%, and when a sample returned to the original position after being subjected to a 50% elongation, the sample was immediately followed by the next motion. Incidentally, the measurement was conducted in the machine direction (MD) and the cross direction (CD) of the nonwoven fabric, respectively.

(10) Stress at Elongation and Stress at Recovery

In the measurement of the recovery after 50% elongation in (9), the stress at 25% elongation in 50% elongation was regarded as the elongation stress (X) and the stress at 25% elongation in recovery after 50% elongation was regarded as the recovery stress (Y). The ratio (Y/X) was calculated from the measured results. Incidentally, the measurement was conducted in the machine direction (MD) and the cross direction (CD) of the nonwoven fabric, respectively.

(11) Curved Ratio of Fiber and Uniformity Thereof

The cross section of the nonwoven fabric was photographed with an electron micrograph (100 magnifications). The area in which the fibers were observed was equally divided in a direction perpendicular to the thickness direction into three areas (a surface layer, an inside layer, and a backside layer). The measuring area was defined as an area which was in almost middle of each layer and had a length of not less than 2 mm in the length direction and a width adjusted to allow the area to contain not less than 500 of the measurable fiber pieces. In each measuring area, the distance between the ends (the shortest distance) of each fiber was measured. In addition, the fiber length (the fiber length on the photograph) of the same fiber was measured. That is, in case of an objective fiber having an end protruding from the inside of the nonwoven fabric, the end was simply regarded as an end required to measure the distance between the ends. In case of an objective fiber having an end hiding in the nonwoven fabric, the boundary from which the fiber was visible (the end of the fiber on the photograph) was regarded as an end required to measure the distance between the ends. Providing that among the fibers photographed, a fiber image which did not have a distance between the ends of the not less than 100 μm continuously was not included in the measuring objects. The curved ratio of fiber (L2/L1) [the fiber length (L2) relative to the distance between the ends (L1)] was calculated. Incidentally, the average curved ratio of fiber was calculated for each of the three areas (the surface layer, the inside layer, and the backside layer) obtained by dividing the cross section equally in a direction perpendicular to the thickness direction. In addition, the uniformity of the curved ratio of fiber in the thickness direction was calculated from the proportion of the maximum and minimum curved ratios of fiber of each layer.

Figure 4:
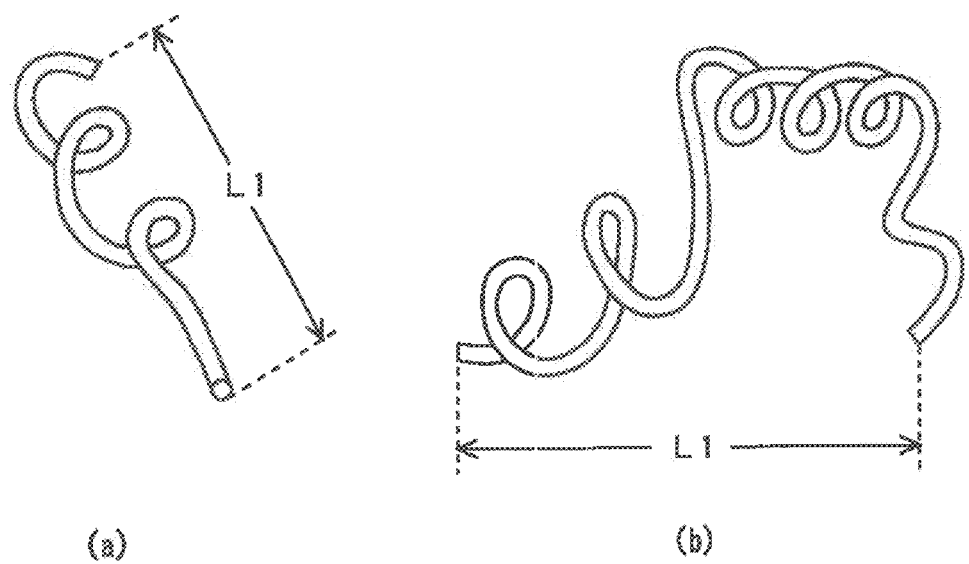
FIG. 4 is a schematic diagram showing a manner of determining a curved ratio of fiber in the present invention.

FIG. 4 illustrates a schematic diagram of the manner of measuring the distance between the ends of the fiber photographed (or the fiber on the photograph). FIG. 4(a) illustrates a fiber having an end protruding from of the inside of the nonwoven fabric and another end hiding in the nonwoven fabric. In this case, the distance L1 between the ends is defined as a distance between the end of the fiber and the boundary from which the fiber hiding in the nonwoven fabric is visible. On the other hand, the fiber length L2 is defined as a length obtained by straightening an observable area of the fiber (an area from an end to another end from which the fiber hiding in the nonwoven fabric is visible) two-dimensionally on the photograph.

FIG. 4(b) illustrates a fiber having both ends hiding in the nonwoven fabric. In this case, the distance L1 between the ends is defined as a distance measured between the boundaries from which the fiber hiding in the nonwoven fabric is visible (the both ends observed on the photograph). On the other hand, the fiber length L2 is defined as a length obtained by straightening an area of the fiber protruding from the inside of the nonwoven fabric.

(12) Proportion of Crimped Fiber Having a Loop (or Coil-Like Crimped Fiber) Observed in Nonowoven Fabric Surface.

The surface of the nonwoven fabric was photographed with an electron microscope (100 magnifications). The number of the crimped fiber having a loop (the fiber which was helically crimped and had a number of at least one turn) or the number of the coil-like crimped fibers forming the nonwoven fabric surface was counted per 1 cm$^2$ in the nonwoven fabric surface on the photograph. That is, only a fiber easily recognized as a mono-fiber forming a smooth loop was counted as the crimped fiber having a loop. Such a measurement was conducted for each of five areas arbitrary selected, and the average of the number of the crimped fibers having a loop was calculated. The obtained value was round to unit and regarded as the proportion of the crimped fiber having a loop observed in the fiber web surface.

Example 1

A side-by-side form conjugated staple fiber (manufactured by Kuraray Co., Ltd., "PN-780", 1.7 dtex×51 mm in length, the number of mechanical crimps was 12/25 mm, and the number of crimps was 62/25 mm after a heat treatment at 130° C. for 1 minute) was prepared as a potential crimping fiber. The conjugated fiber comprised a polyethylene terephthalate resin (A component) having an intrinsic viscosity of 0.65 and a modified polyethylene terephthalate resin (B component). The B component had been obtained by copolymerizing a polyethylene terephthalate resin the same as the A component with 20 mol % of isophthalic acid and 5 mol % of diethylene glycol. Using 100% by mass of the side-by-side form conjugated staple fiber, a card web having a basic weight of 32.1 g/m$^2$ was produced by a carding.

The resulting card web was transferred, being on the conveyor net, to pass through a clearance between the conveyor net and a porous plate drum having pores (circular form) having a diameter of 2 mm and a pitch of 2 mm and arranged in a hound's-tooth check pattern. When the card web was passing therethrough, a water flow was ejected at a pressure of 0.8 MPa from the inside of the porous plate drum toward the web and conveyor net. The card web was moisturized to change the positions of the fibers slightly, without producing fiber entanglements substantially.

The moisturized card web was transferred on a belt conveyor equipped with a 30-mesh endless belt made of a resin and having a width of 500 mm. The web was overfed at a rate of about 200% to allow the web to contract smoothly in the next water vapor treatment step. Incidentally, a pair of belt conveyors used for over feeding the web comprised a first belt conveyor and a second belt conveyor which was the same as the first one and disposed above the first one. The first and second belt conveyors revolved at the same speed rate in the same direction, and the clearance therebetween was adjustable arbitrarily.

Then the card web was introduced to a water vapor spray apparatus disposed behind the belt conveyor. The card web was subjected to a water vapor treatment by spraying the card web perpendicularly with a water vapor ejected at a pressure of 0.4 MPa from the water vapor spray apparatus. In the water vapor treatment, the coil-like crimp and entanglement of the potential crimping fibers were developed at the same time, and a nonwoven fabric was obtained. The water vapor spray apparatus, which was disposed behind the first conveyor, was equipped with a nozzle to eject a water vapor toward the web through the conveyor belt, and a suction apparatus was disposed behind the second conveyor. However, the suction apparatus was not actuated. Incidentally, the water vapor spray apparatus used had a nozzle having a pore size of 0.3 mm, arranged in a line parallel to the width direction of the conveyor in a pitch of 2 mm. The treatment speed was 10 m/minute and the distance between the nozzle and the conveyor belt behind which the suction apparatus was disposed was 10 mm.

The obtained nonwoven fabric had a basic weight of 75.5 g/m$^2$. The nonwoven fabric had a high stretchability in the machine direction (MD) and cross direction (CD), respectively. In addition, the nonwoven fabric was stretched by hand but was not torn, and right after releasing the stress, the deformed nonwoven fabric restored its original form. The results are shown in Table 1. The nonwoven fabric was slit in a width of 5 cm in the length direction, allowing the machine direction (MD) to correspond to the length direction of an objective nonwoven fabric. The resulting nonwoven fabric was rolled up to produce a stretchable and self-fastenable bandage of the present invention. After wrapping the obtained bandage around a finger about three times, the bandage was strongly stretched by hand at the place to be torn. The bandage was easily torn. The bandage end produced by tearing by hand was firmly fastened on the underlying nonwoven fabric which had been wrapped around the finger.

Figure 5:
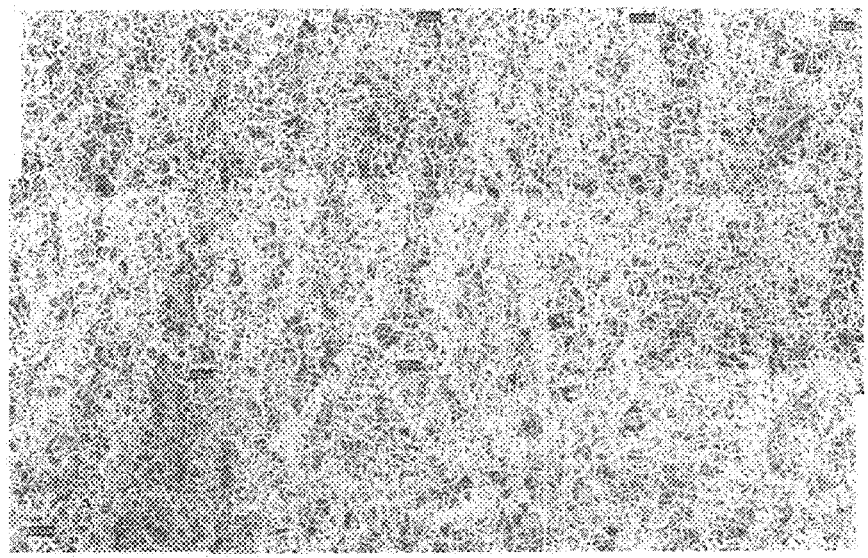
FIG. 5 is an electron micrograph (100 magnifications) of the surface of the nonwoven fabric obtained in Example 1.
Figure 6:
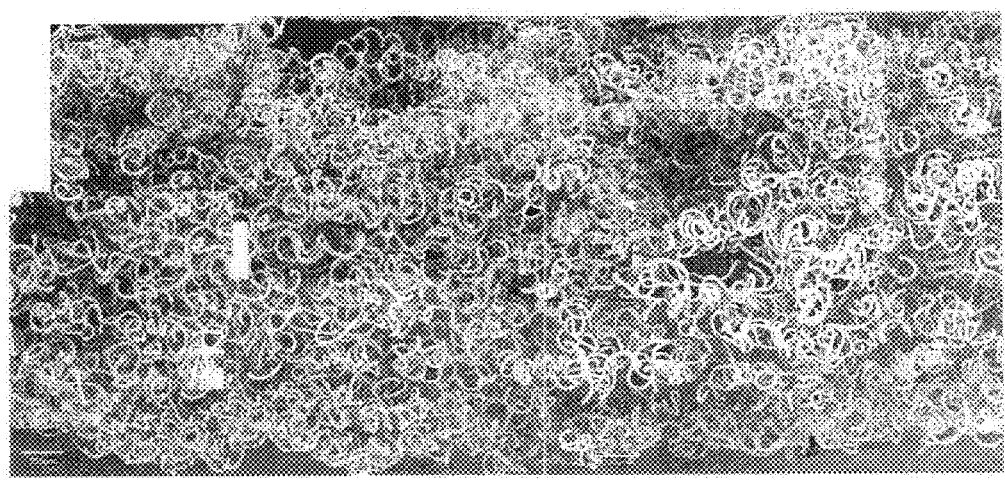
FIG. 6 is an electron micrograph (100 magnifications) of the cross section with respect to the thickness direction of the nonwoven fabric obtained in Example 1.

FIG. 5 is a photograph of the surface of the obtained nonwoven fabric which was taken by an electron microscope (100 magnifications). In addition, FIG. 6 is a photograph of the cross section with respect to the thickness direction of the obtained nonwoven fabric which was taken by an electron microscope (100 magnifications). As apparent from FIGS. 5 and 6, in the nonwoven fabric obtained in Example 1, the crimps having an approximately coil form were uniformly distributed in the thickness direction of the nonwoven fabric and the length direction of each fiber was arranged in a direction parallel to the surface direction of the nonwoven fabric. The results of the evaluation of the obtained nonwoven fabric are shown in Tables 1 to 3.

Example 2

Except for a water pressure of 1.2 MPa at which a water flow was ejected to the card web used in Example 1 when passing through the clearance between the porous plate drum and the net as in Example 1, a nonwoven fabric was obtained by the same manner as in Example 1. The obtained nonwoven fabric has a basic weight of 68.3 g/m$^2$. The nonwoven fabric also had a high stretchability in the machine direction (MD) and cross direction (CD), respectively. The nonwoven fabric was stretched by hand but was not torn, and right after releasing the stress, the deformed nonwoven fabric restored its original form. The results are shown in Table 1. The nonwoven fabric was slit in a width of 5 cm in the length direction. The resulting nonwoven fabric was rolled up to produce a bandage of the present invention. After wrapping the obtained bandage around a finger about three times, the bandage was strongly stretched by hand at the place to be torn. The bandage was torn. The bandage end produced by tearing was fastened on the underlying nonwoven fabric which had been wrapped around the finger.

The observation of the nonwoven fabric obtained in Example 2 by an electron microscope also showed that the crimps having an approximately coil form were uniformly distributed in the thickness direction of the nonwoven fabric and the length direction of each fiber was arranged in a direction parallel to the surface direction of the nonwoven fabric. The results of the evaluation of the obtained nonwoven fabric are shown in Tables 1 to 3.

Example 3

Ninety-five percent by mass of the side-by-side from conjugated staple fiber used in Example 1 and 5% by mass of a polyethylene terephthalate fiber (1.6 dtex×51 mm in length, the number of mechanical crimps was 15/25 mm) were blended. The obtained blend of the fibers was subjected to a carding to produce a card web. The obtained card web had a basic weight of 34.3 g/m$^2$. Except that the web was overfed at a rate of about 120% when being transferred to the belt conveyor, the web was processed by the same manner as in Example 1 to produce a nonwoven fabric.

The obtained nonwoven fabric had a basic weight of 62.7 g/m$^2$, which had been increased by contraction. The nonwoven fabric had a high stretchability in the machine direction (MD) and cross direction (CD), respectively. The nonwoven fabric was stretched by hand but was not torn, and right after releasing the stress, the deformed nonwoven fabric restored its original form. The results are shown in Table 1. The nonwoven fabric was slit in a width of 5 cm in the length direction. The resulting nonwoven fabric was rolled up to produce a stretchable and self-fastenable bandage of the present invention. After wrapping the obtained bandage around a finger about three times, the bandage was strongly stretched by hand at the place to be torn. The bandage was torn. The bandage end produced by tearing was fastened on the underlying nonwoven fabric which had been wrapped around the finger.

The observation of the nonwoven fabric obtained in Example 3 by an electron microscope also showed that the crimps having an approximately coil form were uniformly distributed in the thickness direction of the nonwoven fabric and the length direction of each fiber was arranged in a direction parallel to the surface direction of the nonwoven fabric. The results of the evaluation of the obtained nonwoven fabric are shown in Tables 1 to 3.

Example 4

Using 100% by mass of a side-by side from conjugated staple fiber (1.7 dtex×51 mm in length, the number of mechanical crimps was 12/inch, the number of crimps was 74/25 mm after a heat treatment at 130° C. for 1 minute) as a potential crimping fiber, a card web having a basic weight of 38.3 g/m$^2$ was produced by the same manner as in Example 1. Incidentally, the conjugated fiber comprised a polyethylene terephthalate resin having an intrinsic viscosity of 0.65 (A component) and a modified polyethylene terephthalate resin (B component). The B component had been obtained by copolymerizing a polyethylene terephthalate resin the same as the A component with 30 mol % of isophthalic acid and 7 mol % of diethylene glycol. The card web was processed by the same manner as in Example 1 to produce a nonwoven fabric.

The obtained nonwoven fabric had a basic weight of 108.0 g/m$^2$. The nonwoven fabric had a high stretchability in the machine direction (MD) and cross direction (CD), respectively. The nonwoven fabric was stretched by hand but was not torn, and right after releasing the stress, the deformed nonwoven fabric restored its original form. The results are shown in Table 1. The nonwoven fabric was slit in a width of 5 cm in the length direction. The resulting nonwoven fabric was rolled up to produce a stretchable and self-fastenable bandage of the present invention. After wrapping the obtained bandage around a finger about three times, the bandage was strongly stretched by hand at the place to be torn. The bandage was torn at once. The bandage end produced by tearing was fastened on the underlying nonwoven fabric which had been wrapped around the finger.

The observation of the nonwoven fabric obtained in Example 4 by an electron microscope also showed that the crimps having an approximately coil form were uniformly distributed in the thickness direction of the nonwoven fabric and the length direction of each fiber was arranged in a direction parallel to the surface direction of the nonwoven fabric. The results of the evaluation of the obtained nonwoven fabric are shown in Tables 1 to 3.

Example 5

Using 100% by mass of a side-by side form conjugated staple fiber (1.7 dtex×51 mm in length, the number of mechanical crimps was 12/inch, the number of crimps was 48/25 mm after a heat treatment at 130° C. for 1 minute) as a potential crimping fiber, a card web having a basic weight of 33.4 g/m² was produced by the same manner as in Example 1. Incidentally, the conjugated fiber comprised a polyethylene terephthalate resin having an intrinsic viscosity of 0.65 (A component) and a modified polyethylene terephthalate resin (B component). The B component had been obtained by copolymerizing a polyethylene terephthalate resin the same as the A component with 30 mol % of isophthalic acid and 7 mol % of diethylene glycol. The card web was processed by the same manner as in Example 1 to produce a nonwoven fabric.

The obtained nonwoven fabric had a basic weight of 58.1 g/m². The nonwoven fabric had a high stretchability in the machine direction (MD) and cross direction (CD), respectively. The nonwoven fabric was stretched by hand but was not torn, and right after releasing the stress, the deformed nonwoven fabric restored its original form. The results are shown in Table 1. The nonwoven fabric was slit in a width of 5 cm in the length direction. The resulting nonwoven fabric was rolled up to produce a stretchable and self-fastenable bandage of the present invention. After wrapping the obtained bandage around a finger about three times, the bandage was strongly stretched by hand at the place to be torn. The bandage was torn. The bandage end produced by tearing was fastened on the underlying nonwoven fabric which had been wrapped around the finger.

The observation of the nonwoven fabric obtained in Example 5 by an electron microscope also showed that the crimps having an approximately coil form were uniformly distributed in the thickness direction of the nonwoven fabric and the length direction of each fiber was arranged in a direction parallel to the surface direction of the nonwoven fabric. The results of the evaluation of the obtained nonwoven fabric are shown in Tables 1 to 3.

Example 6

Except for using a card web having a basic weight of 18.3 g/m² produced by carding 100% by mass of the side-by-side form conjugated staple fiber used in Example 1, a nonwoven fabric was produced in the same manner as in Example 1. The obtained nonwoven fabric had a basic weight of 40.2 g/m². The nonwoven fabric had a high stretchability in the machine direction (MD) and cross direction (CD), respectively. The nonwoven fabric was stretched by hand but was not torn, and right after releasing the stress, the deformed nonwoven fabric restored its original form. The results are shown in Table 1. The nonwoven fabric was slit in a width of 5 cm in the length direction. The resulting nonwoven fabric was rolled up to produce a stretchable and self-fastenable bandage of the present invention. After wrapping the obtained bandage around a finger about three times, the bandage was strongly stretched by hand at the place to be torn. The bandage was torn. The bandage end produced by tearing was fastened on the underlying nonwoven fabric which had been wrapped around the finger.

The observation of the nonwoven fabric obtained in Example 6 by an electron microscope also showed that the crimps having an approximately coil form were uniformly distributed in the thickness direction of the nonwoven fabric and the length direction of each fiber was arranged in a direction parallel to the surface direction of the nonwoven fabric. The results of the evaluation of the obtained nonwoven fabric are shown in Tables 1 to 3.

Example 7

Except for using a card web having a basic weight of 76.8 g/m² produced by carding 100% by mass of the side-by-side form conjugated staple fiber used in Example 1, a nonwoven fabric was produced in the same manner as in Example 1. The obtained nonwoven fabric had a basic weight of 150.3 g/m². The nonwoven fabric had a high stretchability in the machine direction (MD) and cross direction (CD), respectively. The nonwoven fabric was stretched by hand but was not torn, and right after releasing the stress, the deformed nonwoven fabric restored its original form. The results are shown in Table 1. The nonwoven fabric was slit in a width of 5 cm in the length direction. The resulting nonwoven fabric was rolled up to produce a stretchable and self-fastenable bandage of the present invention. After wrapping the obtained bandage around a finger about three times, the bandage was strongly stretched by hand at the place to be torn. The bandage was torn. The bandage end produced by tearing was fastened on the underlying nonwoven fabric which had been wrapped around the finger.

The observation of the nonwoven fabric obtained in Example 7 by an electron microscope also showed that the crimps having an approximately coil form were uniformly distributed in the thickness direction of the nonwoven fabric and the length direction of each fiber was arranged in a direction parallel to the surface direction of the nonwoven fabric. The results of the evaluation of the obtained nonwoven fabric are shown in Tables 1 to 3.

Example 8

Except for the water vapor ejection pressure of 1.2 MPa, a nonwoven fabric was obtained by the same manner as in Example 1. The obtained nonwoven fabric had a basic weight of 79.3 g/m². The nonwoven fabric had a high stretchability in the machine direction (MD) and cross direction (CD), respectively. The nonwoven fabric was stretched by hand but was not torn, and right after releasing the stress, the deformed nonwoven fabric restored its original form. The results are shown in Table 1. The nonwoven fabric was slit in a width of 5 cm in the length direction. The resulting nonwoven fabric was rolled up to produce a stretchable and self-fastenable bandage of the present invention. After wrapping the obtained bandage around a finger about three times, the bandage was strongly stretched by hand at the place to be torn. The bandage was torn. The bandage end produced by tearing was fastened on the underlying nonwoven fabric which had been wrapped around the finger.

The observation of the nonwoven fabric obtained in Example 8 by an electron microscope also showed that the crimps having an approximately coil form were uniformly distributed in the thickness direction of the nonwoven fabric and the length direction of each fiber was arranged in a direction parallel to the surface direction of the nonwoven fabric. The results of the evaluation of the obtained nonwoven fabric are shown in Tables 1 to 3.

Comparative Example 1

Using a card web having a basic weight of 32.3 g/m² and comprising 100% by mass of a polyethylene terephthalate fiber (1.6 dtex×51 mm in length, the number of mechanical crimps was 15/25 mm), an attempt to produce a nonwoven fabric by the same manner as in Example 1 was made. Although the card web was exposed to a water vapor, the crimps of the fibers did not develop. Since the state of the card web almost unchanged, a nonwoven fabric which easy to convey directly to the next step was not able to be obtained.

Comparative Example 2

One surface of the card web used in Example 1 was subjected to a hydroentangling using a nozzle having a pore size of ϕ0.1 mm under the condition that the water pressure of a first orifice line was 2.9 MPa and the water pressure of a second orifice line was 3.9 MPa (which was a common condition for a hydroentangling). Then the resulting web was subjected to a heat treatment in a hot air dryer having a temperature of 130° C. to develop the crimps of the fibers of the web. The obtained nonwoven fabric had stretchability. However, the nonwoven fabric evidently had a low recovery stress. The nonwoven fabric was slit in a width of 5 cm in the length direction. The resulting nonwoven fabric was rolled up to produce a bandage. After wrapping the obtained bandage around a finger about three times, the bandage was strongly stretched by hand at the place to be torn. The nonwoven fabric was torn with a great effort since the bandage had a high strength. Furthermore, the bandage end produced by tearing by hand was not fastened on the underlying nonwoven fabric which had been wrapped around the finger.

The observation of the nonwoven fabric obtained in Comparative Example 2 by an electron microscope was as follows: owing to the hot air treatment of the nonwoven fabric, in the middle area with respect to the thickness direction of the nonwoven fabric the coil-like crimps of each fiber were insufficiently developed and across the thickness direction the degree of crimping of each fiber was ununiform; and a large amount of the fibers whose fiber length directions were arranged in a direction perpendicular to the surface direction. The results of the evaluation of the obtained nonwoven fabric are shown in Tables 1 to 3.

Comparative Example 3

One surface of the card web used in Example 1 was subjected to a hydroentangling using a nozzle having a pore size of ϕ0.1 mm under the condition that the water pressure of a first orifice line was 2.9 MPa and the water pressure of a second orifice line was 3.9 MPa (which was a condition for a common hydroentangling). As in Example 1, the resulting web was overfed into a water vapor spray apparatus disposed behind the belt conveyor, paying attention not to inhibit the compression of the web. The web was then subjected to a water vapor treatment by spraying the card web with a water vapor ejected at a pressure of 0.4 MPa from the water vapor spray apparatus perpendicular to the web. In the water vapor treatment, the coil-like crimps of the potential crimping fibers were developed and the fibers were simultaneously entangled with each other, and a nonwoven fabric was obtained. Incidentally, the conditions of the water vapor spray nozzle, the processing speed, and the distance between the nozzle and the conveyor belt equipped with the suction apparatus or box were the same as in Example 1. The nonwoven fabric was slit in a width of 5 cm in the length direction. The resulting nonwoven fabric was rolled up to produce a stretchable and self-fastenable bandage of the present invention. After wrapping the obtained bandage around a finger about three times, the bandage was strongly stretched by hand at the place to be torn. The nonwoven fabric was torn with a great effort since the bandage had a high strength. Furthermore, the bandage end produced by tearing was not firmly fastened on the underlying nonwoven fabric which had been wrapped around the finger and immediately unfastened.

Figure 7:
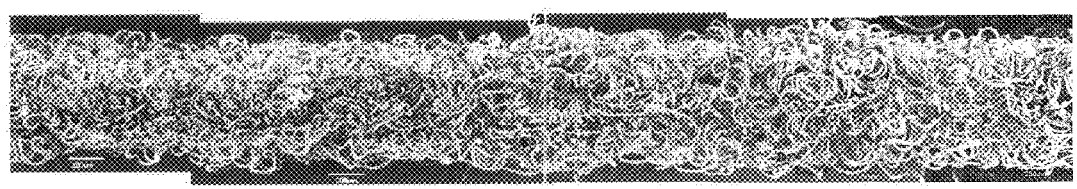
FIG. 7 is an electron micrograph (100 magnifications) of the cross section with respect to the thickness direction of the nonwoven fabric obtained in Comparative Example 3.

FIG. 7 is a photograph of the cross section with respect to the thickness direction of the obtained nonwoven fabric, which was taken by an electron microscope (100 magnifications). As apparent from FIG. 7, the approximately coil form crimps of each fiber of the nonwoven fabric obtained in Comparative Example 3 were distributed uniformly in the thickness direction of the nonwoven fabric. However, the observation revealed that a large number of the fibers whose fiber length direction was arranged in a direction perpendicular to the surface direction of the nonwoven fabric due to the entanglement of the fibers under the condition for a common hydroentngling. The results of the evaluation of the obtained nonwoven fabric are shown in Tables 1 to 3.

Comparative Example 4

Except for using a card web having a basic weight of 31.5 g/m$^2$ produced using 100% by mass of a side-by side form conjugated staple fiber (1.7 dtex×51 mm in length, the number of mechanical crimps was 12/25 mm, the number of crimps was 26/25 mm after a heat treatment at 130° C. for 1 minute) as a potential crimping fiber, a nonwoven fabric was produced in the same manner as in Example 1. Incidentally, the conjugated fiber comprised a polyethylene terephthalate resin having an intrinsic viscosity of 0.65 (A component) and a modified polyethylene terephthalate resin (B component). The B component had been obtained by copolymerizing a polyethylene terephthalate resin the same as the A component with 10 mol % of isophthalic acid.

The obtained nonwoven fabric had a basic weight of 42.2 g/m$^2$. The nonwoven fabric evidently had a low recovery after elongation, judging by touching the nonwoven fabric. The nonwoven fabric was slit in a width of 5 cm in the length direction. The resulting nonwoven fabric was rolled up to produce a bandage. After wrapping the obtained bandage around a finger about three times, the bandage was strongly stretched by hand at the place to be torn. The bandage was torn. Although the bandage end produced by tearing by hand was fastened on the underlying nonwoven fabric which had been wrapped around the finger, the bandage end immediately unfastened when the hand moved.

The observation of the nonwoven fabric obtained in Comparative Example 4 by an electron microscope was as follows: the crimps of each fiber of the nonwoven fabric were uniformly distributed in the thickness direction and the length direction of each fiber was arranged in a direction to almost parallel to the surface direction of the nonwoven fabric. However, the observation also revealed an insufficient degree of crimping of the fiber and a large diameter of the crimps. The results of the evaluation of the obtained nonwoven fabric are shown in Tables 1 to 3.

Reference Example

Using a commercially available self-adhesive bandage (manufactured by Johnson & Johnson, "BAND-AID (registered trademark) Koredake kantan houtai (stretch type) 5 cm-width"), the stretchability and fastenability, which is achieved by virtue of adhesive agent, were determined by the same manner as in the present invention. The bandage had an uneven surface which provided stretchability, and the surface was coated with an adhesive agent comprising a non-natural rubber component in order to provide self-adhesiveness. Incidentally, the measuring samples of the bandage had the length direction corresponding to the machine direction (MD) of the bandage. The results are shown in Table 1. The results of the measurements show that the bandage had a high recovery after 50% elongation, which was 99%, and a high slip stress at curved surfaces in contact, which was evaluated as "broken". However, in a practical use it required a lot of effort to tear the bandage by stretching at the place to be torn after wrapping the bandage around a finger. In addition, since the surface of the bandage was coated with the adhesive agent, a dust or dirt was adhered on or attached to the surface of the bandage during its use.

TABLE 1

|  | Physical properties of crimping fiber | Physical properties of nonwoven fabric | | | | | | |
|---|---|---|---|---|---|---|---|---|
|  |  | Basic | | | Strength at break | | Elongation at break | |
|  | Average curvature radius (µm) | weight (g/m²) | Thickness (mm) | Density (g/cm³) | MD (N/50 mm) | CD | MD (%) | CD |
| Example 1 | 81 | 75.5 | 0.82 | 0.092 | 7.0 | 0.3 | 132 | 144 |
| Example 2 | 127 | 68.3 | 0.77 | 0.089 | 6.5 | 0.7 | 73 | 127 |
| Example 3 | 146 | 62.7 | 0.76 | 0.083 | 6.2 | 2.7 | 89 | 135 |
| Example 4 | 72 | 108.0 | 1.10 | 0.098 | 12.1 | 2.4 | 99 | 220 |
| Example 5 | 192 | 58.1 | 0.64 | 0.091 | 5.7 | 2.1 | 98 | 107 |
| Example 6 | 97 | 40.2 | 0.47 | 0.086 | 5.2 | 1.8 | 87 | 93 |
| Example 7 | 93 | 150.3 | 1.26 | 0.119 | 18.1 | 6.7 | 138 | 145 |
| Example 8 | 82 | 79.3 | 0.85 | 0.093 | 7.1 | 3.3 | 142 | 149 |
| Comparative Example 1 | Impossible to produce nonwoven fabric | | | | | | | |
| Comparative Example 2 | 182 | 60.8 | 0.49 | 0.124 | 39.8 | 36.9 | 162 | 203 |
| Comparative Example 3 | 156 | 77.5 | 0.68 | 0.114 | 33.3 | 9.6 | 172 | 203 |
| Comparative Example 4 | 310 | 42.2 | 0.91 | 0.076 | 3.9 | 1.6 | 85 | 98 |
| Reference Example | — | 145.9 | 1.70 | 0.086 | 60.9 | — | 245 | — |

TABLE 2

|  | Physical properties of nonwoven fabric Stretchability (behavior in recovery after 50% elongation) | | | | | | | |
|---|---|---|---|---|---|---|---|---|
|  | Recovery after elongation | Elongation stress (X) | Recovery stress (Y) | Y/X | Recovery after elongation | Elongation stress (X) | Recovery stress (Y) | Y/X |
|  | MD | | | | CD | | | |
|  | (%) | (N/50 mm) | (N/50 mm) | — | (%) | (N/50 mm) | (N/50 mm) | — |
| Example 1 | 100 | 1.17 | 0.67 | 0.57 | 98 | 0.34 | 0.33 | 0.97 |
| Example 2 | 86 | 1.86 | 0.46 | 0.25 | 93 | 0.54 | 0.28 | 0.52 |
| Example 3 | 89 | 0.82 | 0.35 | 0.43 | 89 | 0.26 | 0.12 | 0.46 |
| Example 4 | 100 | 3.21 | 2.03 | 0.63 | 99 | 0.32 | 0.21 | 0.66 |
| Example 5 | 85 | 0.79 | 0.26 | 0.33 | 81 | 0.15 | 0.10 | 0.67 |
| Example 6 | 84 | 0.61 | 0.11 | 0.18 | 81 | 0.08 | 0.07 | 0.88 |
| Example 7 | 97 | 2.03 | 0.95 | 0.47 | 94 | 0.49 | 0.34 | 0.69 |
| Example 8 | 99 | 1.22 | 0.65 | 0.53 | 98 | 0.26 | 0.18 | 0.69 |
| Comparative Example 1 | Impossible to produce nonwoven fabric | | | | | | | |
| Comparative Example 2 | 78 | 4.27 | 0.08 | 0.02 | 75 | 4.18 | 0 | 0 |
| Comparative Example 3 | 83 | 6.12 | 0.59 | 0.10 | 85 | 1.18 | 0.41 | 0.35 |
| Comparative Example 4 | 78 | 0.59 | 0 | 0 | 71 | 0.09 | 0 | 0 |
| Reference Example | 99 | 0.32 | 0.17 | 0.53 | — | — | — | — |

TABLE 3

|  | Physical properties of nonwoven fabric | | | | | | |
|---|---|---|---|---|---|---|---|
|  | Slip stress at curved surfaces in contact | Water repellency | Curved ratio of fiber | | | | Proportion of crimped fiber having a loop in nonwoven fabric surface |
|  | (N/5 cm) | (Score) | Surface area | Middle area | Backside area | Uniformity (%) | (piece/cm²) |
| Example 1 | broken | 4 | 2.25 | 1.98 | 2.28 | 86.8 | 23 |
| Example 2 | broken | 4 | 1.73 | 1.44 | 1.53 | 83.2 | 12 |
| Example 3 | 1.3 | 3 | 1.88 | 1.51 | 1.72 | 80.3 | 18 |
| Example 4 | broken | 4 | 2.81 | 2.60 | 2.85 | 91.2 | 42 |
| Example 5 | 0.8 | 4 | 1.78 | 1.42 | 1.81 | 78.5 | 13 |
| Example 6 | broken | 4 | 2.32 | 2.04 | 2.37 | 86.1 | 21 |
| Example 7 | broken | 4 | 2.21 | 1.78 | 2.22 | 80.2 | 29 |
| Example 8 | 3.4 | 4 | 2.48 | 2.37 | 2.52 | 94.0 | 46 |
| Comparative Example 1 | Impossible to produce nonwoven fabric | | | | | | |
| Comparative Example 2 | 0 | 2 | 1.53 | 1.09 | 1.49 | 71.2 | 4 |

TABLE 3-continued

| | Physical properties of nonwoven fabric | | | | | | |
|---|---|---|---|---|---|---|---|
| | Slip stress at curved surfaces in | Water | Curved ratio of fiber | | | | Proportion of crimped fiber having a loop in nonwoven |
| | contact (N/5 cm) | repellency (Score) | Surface area | Middle area | Backside area | Uniniformity (%) | fabric surface (piece/cm$^2$) |
| Comparative Example 3 | 0 | 4 | 1.66 | 1.26 | 1.52 | 75.9 | 9 |
| Comparative Example 4 | 0.4 | 4 | 2.25 | 1.98 | 2.28 | 86.8 | 7 |
| Reference Example | broken | 2 | — | — | — | — | — |

The results of Tables 1 to 3 show that the stretchable and self-fastenable bandage of the present invention has a self-fastenability similar to the self-adhesiveness which a conventional bandage using an adhesive agent achieves, in addition to an excellent stretchability and tearability by hand.

Comparative Example 5

The card web used in Example 1 was subjected to a heat treatment at 130° C. for 3 minutes in a hot air dryer to develop the coil-like crimps of the fibers. The observation of the surface of the obtained nonwoven fabric having a crimp developed by the above-mentioned manner revealed an irregular texture formed by the high-density portions and low-density portions of the fibers in an islands-in-sea form. Incidentally, the irregular texture differed from the density difference formed by using the porous plate drum in Example. The high-density portions or the low-density portions had a diameter of about 10 mm ϕ and irregularly distributed in the nonwoven fabric, whereby the nonwoven fabric had an extremely poor appearance. When the nonwoven fabric was strongly stretched at the place to be torn after the nonwoven fabric was wrapped around a finger about three times as in Example 1, the nonwoven fabric was torn without showing a slight elongation. The nonwoven fabric was fastened by overlapping the end produced by tearing the nonwoven fabric in place on the underlying nonwoven fabric. However, since the nonwoven fabric was loosely fastened and not so tight fitting, when the finger was slowly moved, not only the rolled nonwoven fabric was almost slipped from the finger, but also the end fastened on the underlying nonwoven fabric became peeled.

Presumably, the reason for such a phenomenon is as follows: the crimp development of the fibers due to the use of the hot air having a low thermal conductivity and an ability of passing through the web freely allows the fibers aggregated before the water vapor treatment to increase the entanglement of the fiber. At such a fiber entanglement a pulling force is generated, so that the fibers less aggregated before the water vapor treatment is pulled in directions opposite to each other.

On the other hand, as in Examples, the high-temperature water vapor was used to fix the fibers of the nonwoven fabric, being restrained, and the nonwoven fabric contracted. Moreover, presumably, owing to the higher thermal conductivity of the high-temperature water vapor than that of the hot air, the construction of the nonwoven fabric was sufficiently developed, with fixing the fibers, which led to a more uniform construction compared with the construction by the hot air. Such a construction inhibits the generation of an evidently irregular texture caused by the use of the hot air.

The invention claimed is:

1. A nonwoven fabric comprising a conjugated fiber comprising a plurality of resins which are different in thermal shrinkage and which form a phase separation structure, which plurality of resins comprises polyalkylene arylate resin and a modified polyalkylene arylate resin of said polyalkylene arylate resin, which nonwoven fabric is a tape having a ratio of the strength at break in a length direction relative to the strength at break in a width direction of 1.5 to 50,
wherein the conjugated fibers are arranged in a direction approximately parallel to a surface direction of the nonwoven fabric and crimped and the conjugated fibers have an average curvature radius of fiber crimp of 20 to 200 μm, and the crimps are distributed approximately uniformly in a thickness direction of the nonwoven fabric,
wherein an average fiber length of the conjugated fiber is 10 to 100 mm,
wherein the nonwoven fabric has a curved ratio of fiber of not less than 1.3 and a proportion of the minimum curved ratio of fiber relative to the maximum curved ratio of fiber of not less than 75% in each of three areas, providing that the nonwoven fabric is cut across the thickness direction and the cross section is divided in a direction perpendicular to the thickness direction equally into three, and
wherein the nonwoven fabric is obtained by a process comprising
forming a web with a fiber including said conjugated fiber, and
heating the resulting fiber web with a high-temperature water vapor to allow the conjugated fiber to develop a crimp having an average curvature radius of 20 to 200 μm, wherein the temperature of the high-temperature water vapor is about 70 to 150° C.

2. The nonwoven fabric according to claim 1, wherein the plurality of resins comprise a non thermal adhesive resin under moisture which has a softening point or melting point of not lower than 100° C. and forms at least a portion of a surface of the conjugated fiber.

3. The nonwoven fabric according to claim 1, which is substantially free from an adhesive agent, wherein each fiber is substantially not melt-bonded to another.

4. The nonwoven fabric according to claim 1, wherein the conjugated fiber has a side-by-side or eccentric sheath-core form.

5. The nonwoven fabric according to claim 1, which further comprises non-conjugated fibers, and wherein a proportion of the conjugated fiber is not less than 80% by mass relative to total amount of the conjugated fiber and the non-conjugated fibers.

6. The nonwoven fabric according to claim 1, which has a plurality of low-density portions and a plurality of high-density portions in a surface direction, wherein the low-density portion and the high-density portion are alternately formed in a periodic pattern.

7. The nonwoven fabric according to claim 1, which has a strength at break of 5 to 30 N/50 mm, an elongation at break of not less than 50%, a recovery after 50% elongation of not less than 80%, and a slip stress at curved surfaces in contact of not less than 0.5 N/50 mm, in at least one direction.

8. The nonwoven fabric according to claim 1, wherein the tape is selected from the group consisting of a bandage and a supporter.

9. The nonwoven fabric according to claim 1, wherein the curved ratio of fiber is about 1.4 to 4.

10. The nonwoven fabric according to claim 1, wherein the curved ratio of fiber is about 1.6 to 3.

11. The nonwoven fabric according to claim 1, wherein the curved ratio of fiber is about 1.8 to 2.5.

12. The nonwoven fabric according to claim 1, wherein the proportion of the minimum curved ratio of fiber relative to the maximum curved ratio of fiber is about 80 to 99% in each of the three areas.

13. The nonwoven fabric according to claim 1, wherein the proportion of the minimum curved ratio of fiber relative to the maximum curved ratio of fiber is about 82 to 98% in each of the three areas.

14. The nonwoven fabric according to claim 1, wherein the proportion of the minimum curved ratio of fiber relative to the maximum curved ratio of fiber is about 85 to 97% in each of the three areas.

15. The nonwoven fabric according to claim 1, which has a bulk density of about 0.01 to 0.15 g/cm$^3$.

16. The nonwoven fabric according to claim 1, which has a bulk density of about 0.07 to 0.15 g/cm$^3$.

17. The nonwoven fabric according to claim 1, wherein the polyalkylene arylate resin is a homopolymer and the modified polyalkylene arylate resin is a copolymer comprising a copolymerizable component lowering the melting point or softening point, or the degree of crystallization, of the polyalkylene arylate resin.

18. The nonwoven fabric according to claim 17, wherein the copolymerizable component comprises at least one of an asymmetric aromatic dicarboxylic acid and a polyoxyC$_{2-4}$ alkylene glycol.

* * * * *